United States Patent
Feng et al.

(10) Patent No.: US 10,526,659 B2
(45) Date of Patent: Jan. 7, 2020

(54) BIOMARKERS FOR COLORECTAL CANCER

(71) Applicants: BGI Shenzhen Co., Limited, Shenzhen, Guangdong (CN); BGI Shenzhen, Shenzhen, Guangdong (CN)

(72) Inventors: Qiang Feng, Guangdong (CN); Dongya Zhang, Guangdong (CN); Longqing Tang, Guangdong (CN); Jun Wang, Guangdong (CN)

(73) Assignees: BGI Shenzhen Co., Limited, Shenzhen, Guangdong (CN); BGI Shenzhen, Shenzhen, Guangdong (CN)

( * ) Notice: Subject to any disclaimer, the term of this patent is extended or adjusted under 35 U.S.C. 154(b) by 607 days.

(21) Appl. No.: 15/017,087

(22) Filed: Feb. 5, 2016

(65) Prior Publication Data

US 2016/0160296 A1    Jun. 9, 2016

Related U.S. Application Data

(63) Continuation-in-part of application No. PCT/CN2014/083664, filed on Aug. 5, 2014.

(30) Foreign Application Priority Data

Aug. 6, 2013 (WO) ................ PCT/CN2013/080872

(51) Int. Cl.
- *C12Q 1/68* (2018.01)
- *C07H 21/04* (2006.01)
- *C12Q 1/6886* (2018.01)
- *C12Q 1/6806* (2018.01)

(52) U.S. Cl.
CPC ......... *C12Q 1/6886* (2013.01); *C12Q 1/6806* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS 5,474,796 A * 12/1995 Brennan .............. B01J 19/0046
422/547

FOREIGN PATENT DOCUMENTS

| CN | 101988060 A | 3/2011 |
|---|---|---|
| CN | 102936597 A | 2/2013 |
| WO | 2010096154 A2 | 8/2010 |
| WO | 2013052480 A1 | 4/2013 |
| WO | 2015/018308 A1 | 2/2015 |

OTHER PUBLICATIONS

NEB catalog (1998/1999), pp. 121, 284. (Year: 1998).*
Int'l Search Report and Written Opinion dated Nov. 24, 2014 in Int'l Application No. PCT/CN2014/083664.
Wang, T. et al., "Structural segregation of gut microbiota betwen colorectal cancer patients and healthy volunteers," International Society for Microbial Ecology, vol. 6, pp. 320-329 (2011).

* cited by examiner

*Primary Examiner* — Jeanine A Goldberg
(74) *Attorney, Agent, or Firm* — Panitich Schwarze Belisario & Nadel LLP

(57) ABSTRACT

Biomarkers and methods related to microbiota for predicting the risk of a disease, particularly colorectal cancer (CRC), are described.

6 Claims, 9 Drawing Sheets
Specification includes a Sequence Listing.

A

B

BIOMARKERS FOR COLORECTAL CANCER

CROSS-REFERENCE TO RELATED APPLICATION

The present patent application is a continuation-in-part of PCT Patent Application No. PCT/CN2014/083664, filed Aug. 5, 2014, which was published in the English language on Feb. 12, 2015, under International Publication No. WO 2015/018308 A1, which claims priority to PCT Patent Application No. PCT/CN2013/080872, filed Aug. 6, 2013, and the disclosure of both prior applications is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "Sequence_Listing.TXT", creation date of Jan. 26, 2016, and having a size of about 43.7 kilobytes. The sequence listing submitted via EFS-Web is part of the specification and is herein incorporated by reference in its entirety.

FIELD

The present invention relates to biomarkers and methods for predicting the risk of a disease related to microbiota, in particular colorectal cancer (CRC).

BACKGROUND

Colorectal cancer (CRC) is the third most common form of cancer and the second leading cause of cancer-related death in the Western world (Schetter et al., 2011, "Alterations of microRNAs contribute to colon carcinogenesis," *Semin Oncol.*, 38:734-742, incorporated herein by reference). A lot of people are diagnosed with CRC and many patients die of this disease each year worldwide. Although current treatment strategies, including surgery, radiotherapy, and chemotherapy, have a significant clinical value for CRC, the relapses and metastases of cancers after surgery have hampered the success of those treatment modalities. Early diagnosis of CRC will help to not only prevent mortality, but also to reduce the costs for surgical intervention.

Current tests of CRC, such as flexible sigmoidoscopy and colonoscopy, are invasive, and patients may find the procedures and the bowel preparation to be uncomfortable or unpleasant.

The development of CRC is a multifactorial process influenced by genetic, physiological, and environmental factors. With regard to environmental factors, lifestyle, particularly dietary intake, may affect the risk of developing CRC. The Western diet, which is rich in animal fat and poor in fiber, is generally associated with an increased risk of CRC. Thus, it has been hypothesized that the relationship between the diet and CRC, may be due to the influence that the diet has on the colon microbiota and bacterial metabolism, making both the colon microbiota and bacterial metabolism relevant factors in the etiology of the disease (McGarr et al., 2005, "Diet, anaerobic bacterial metabolism, and colon cancer," *J Clin Gastroenterol.*, 39:98-109; Hatakka et al., 2008, "The influence of *Lactobacillus rhamnosus* LC705 together with *Propionibacterium freudenreichii* ssp. *shermanii* JS on potentially carcinogenic bacterial activity in human colon," *Int J Food Microbiol.* 128:406-410, both incorporated herein by reference).

Interactions between the gut microbiota and the immune system have an important role in many diseases both within and outside the gut (Cho et al., 2012, "The human microbiome: at the interface of health and disease," *Nature Rev. Genet.*, 13, 260-270, incorporated herein by reference). Intestinal microbiota analysis of feces DNA has the potential to be used as a noninvasive test for identifying specific biomarkers that can be used as a screening tool for early diagnosis of patients having CRC, thus leading to longer survival and a better quality of life.

With the development of molecular biology and its application in microbial ecology and environmental microbiology, an emerging field of metagenomics (environmental genomics or ecogenomics), has been rapidly developed. Metagenomics, comprising extracting total community DNA, constructing a genomic library, and analyzing the library with similar strategies for functional genomics, provides a powerful tool to study uncultured microorganisms in complex environmental habitats. In recent years, metagenomics has been applied to many environmental samples, such as oceans, soils, rivers, thermal vents, hot springs, and human gastrointestinal tracts, nasal passages, oral cavities, skin and urogenital tracts, illuminating its significant value in various areas including medicine, alternative energy, environmental remediation, biotechnology, agriculture and biodefense. For the study of CRC, the inventors performed analysis in the metagenomics field.

SUMMARY

Embodiments of the present disclosure seek to solve at least one of the problems existing in the prior art to at least some extent.

The present invention is based on at least the following findings by the inventors:

Assessment and characterization of gut microbiota has become a major research area in human disease, including colorectal cancer (CRC), one of the common causes of death among all types of cancers. To carry out analysis on the gut microbial content of CRC patients, the inventors performed deep shotgun sequencing of the gut microbial DNA from 128 Chinese individuals and conducted a Metagenome-Wide Association Study (MGWAS) using a protocol similar to that described by Qin et al., 2012, "A metagenome-wide association study of gut microbiota in type 2 diabetes," *Nature*, 490, 55-60, the entire content of which is incorporated herein by reference. The inventors identified and validated 140,455 CRC-associated gene markers. To test the potential ability to classify CRC via analysis of gut microbiota, the inventors developed a disease classifier system based on 31 gene markers that are defined as an optimal gene set by a minimum redundancy–maximum relevance (mRMR) feature selection method. For intuitive evaluation of the risk of CRC disease based on these 31 gut microbial gene markers, the inventors calculated a healthy index. The inventors' data provide insight into the characteristics of the gut metagenome corresponding to a CRC risk, a model for future studies of the pathophysiological role of the gut metagenome in other relevant disorders, and the potential for a gut-microbiota-based approach for assessment of individuals at risk of such disorders.

It is believed that gene markers of intestinal microbiota are valuable for improving cancer detection at earlier stages for at least the following reasons. First, the markers of the present invention are more specific and sensitive as compared to conventional cancer markers. Second, the analysis of stool samples ensures accuracy, safety, affordability, and patient compliance, and stool samples are transportable. As compared to a colonoscopy, which requires bowel preparation, polymerase chain reaction (PCR)-based assays are comfortable and noninvasive, such that patients are more likely to be willing to participate in the described screening program. Third, the markers of the present invention can also serve as a tool for monitoring therapy of cancer patients in order to measure their responses to therapy.

BRIEF DISCRIPTION OF DRAWINGS

These and other aspects and advantages of the present disclosure will become apparent and more readily appreciated from the following descriptions taken in conjunction with the drawings. It should be understood that the invention is not limited to the precise embodiments shown in the drawings.

In the drawings:

FIG. 1 shows the distribution of P-value association statistics of all the microbial genes analyzed in this study: the association analysis of CRC p-value distribution identified a disproportionate over-representation of strongly associated markers at lower P-values, with the majority of genes following the expected P-value distribution under the null hypothesis, suggesting that the significant markers likely represent true rather than false associations;

FIG. 2 shows minimum redundancy maximum relevance (mRMR) method to identify 31 gene markers that differentiate colorectal cancer cases from controls: an incremental search was performed using the mRMR method which generated a sequential number of subsets; for each subset, the error rate was estimated by a leave-one-out cross-validation (LOOCV) of a linear discrimination classifier; and the optimum subset with the lowest error rate contained 31 gene markers;

FIG. 3 shows the discovered gut microbial gene markers associated with CRC: the CRC indexes computed for the CRC patients and the control individuals from this study are shown along with patients and control individuals from earlier studies on type 2 diabetes and inflammatory bowel disease; the boxes depict the interquartile ranges between the first and third quartiles, and the lines inside the boxes denote the medians; the calculated gut healthy index listed in Table 6 correlated well with the ratio of CRC patients in the population; and the CRC indexes for CRC patient microbiomes are significantly different from the rest (***P<0.001);

FIG. 4 shows that ROC analysis of the CRC index from the 31 gene markers in Chinese cohort I showing excellent classification potential, with an area under the curve of 0.9932;

FIG. 5 shows that the CRC index was calculated for an additional 19 Chinese CRC and 16 non-CRC samples in Example 2: the boxes in the inset depict the interquartile ranges (IQR) between the first and third quartiles (25th and 75th percentiles, respectively) and the lines inside denote the medians, while the points represent the gut healthy indexes in each sample; the squares represent the case group (CRC); the triangles represent the controls group (non-CRC); the triangle with the * represents non-CRC individuals that were diagnosed as CRC patients;

Figure 8:
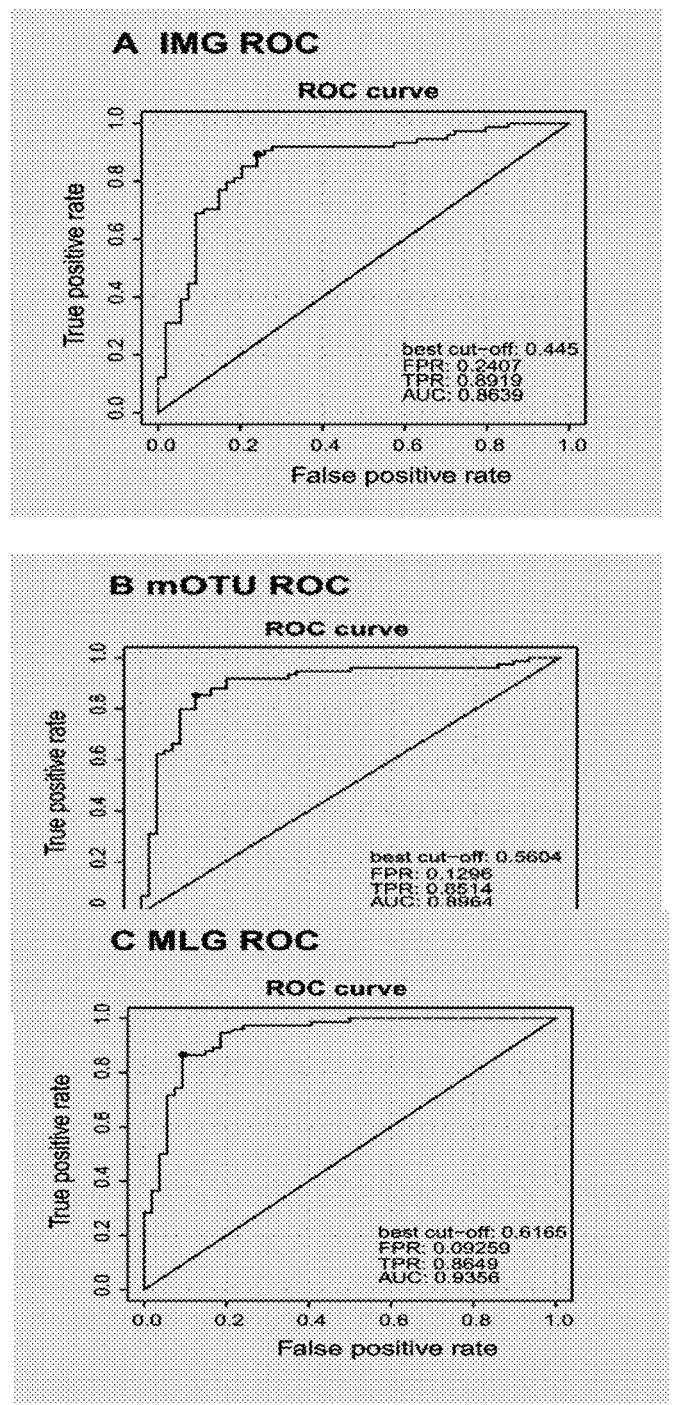
Figure 9:
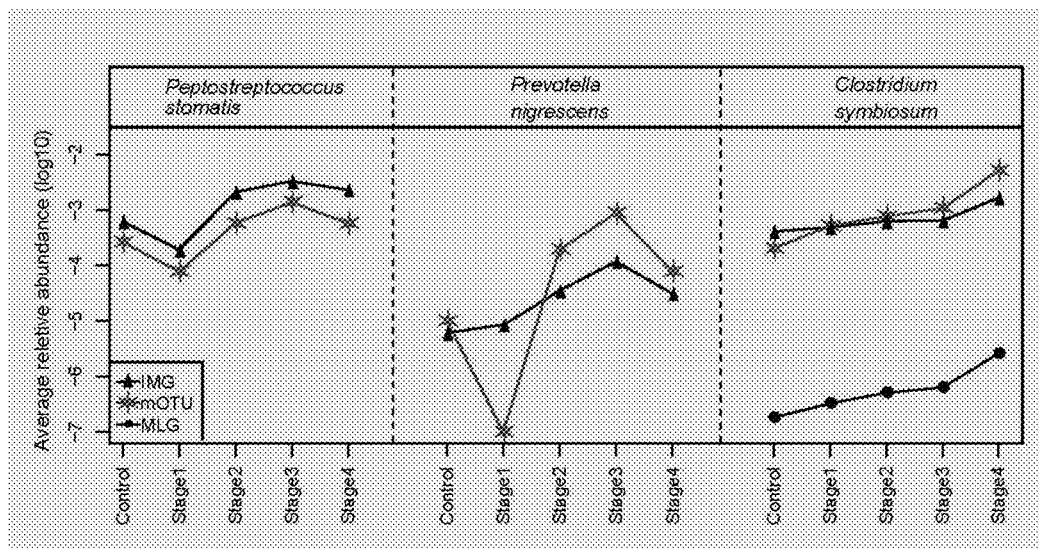
Figure 10:
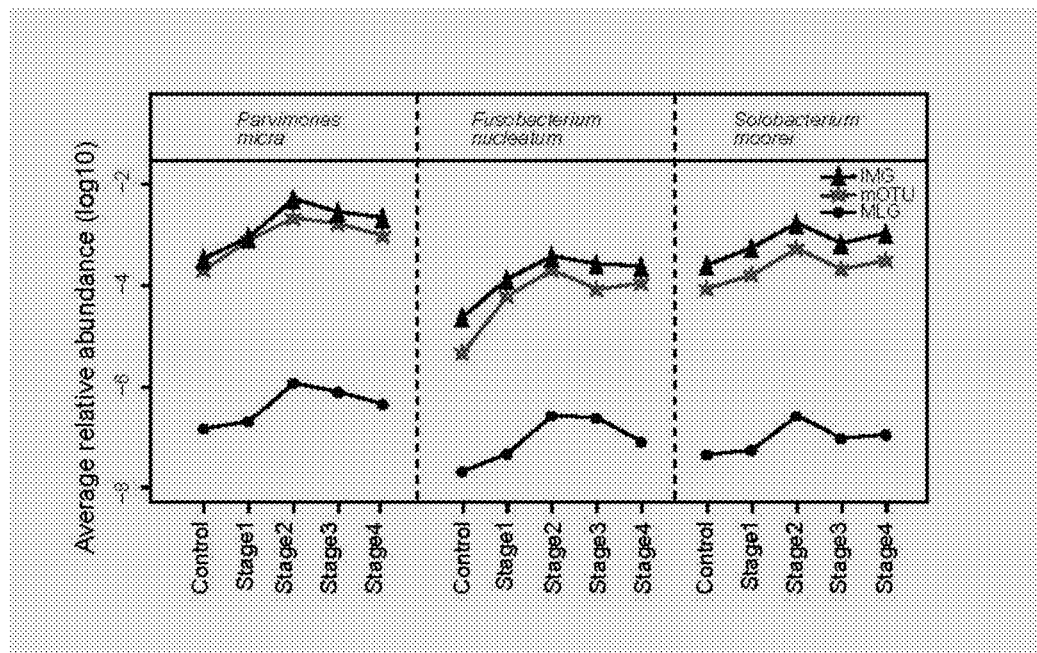
Figure 11:
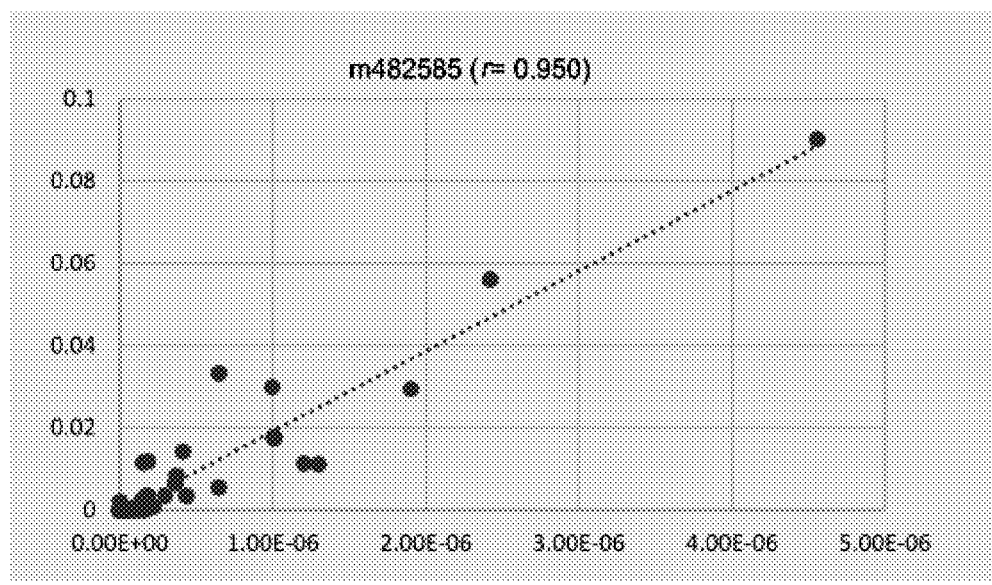
Figure 11:
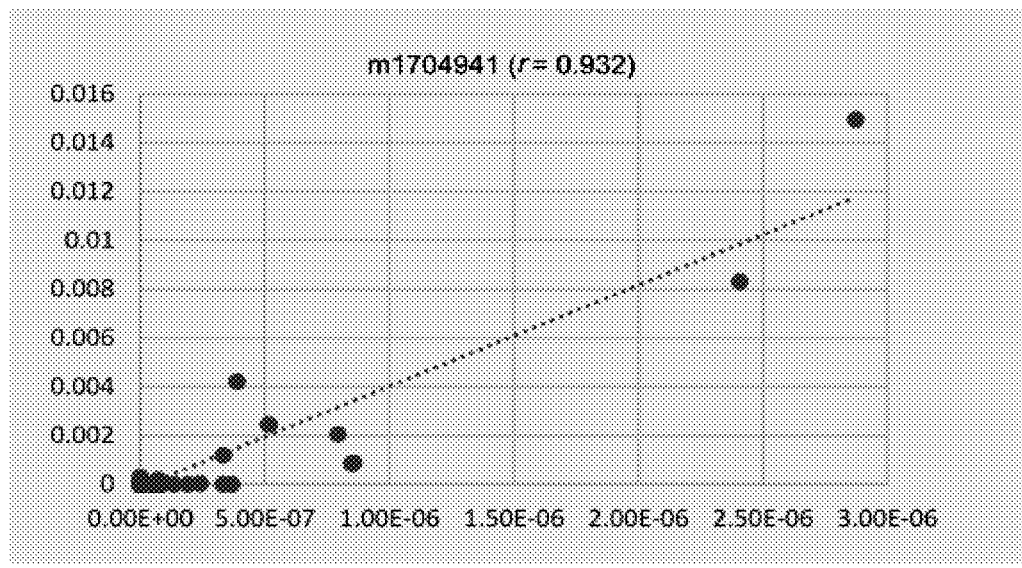
Figure 12:
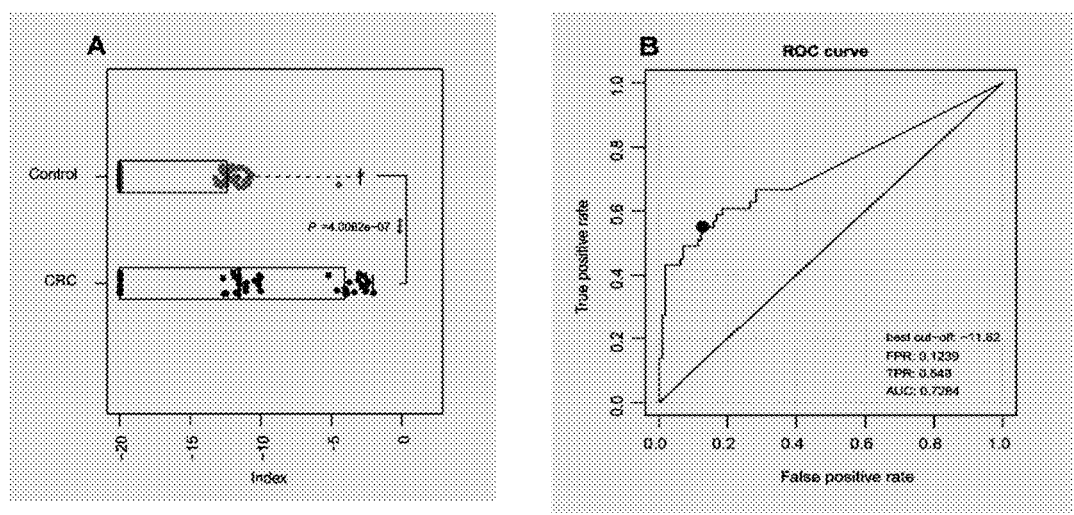
Figure 13:
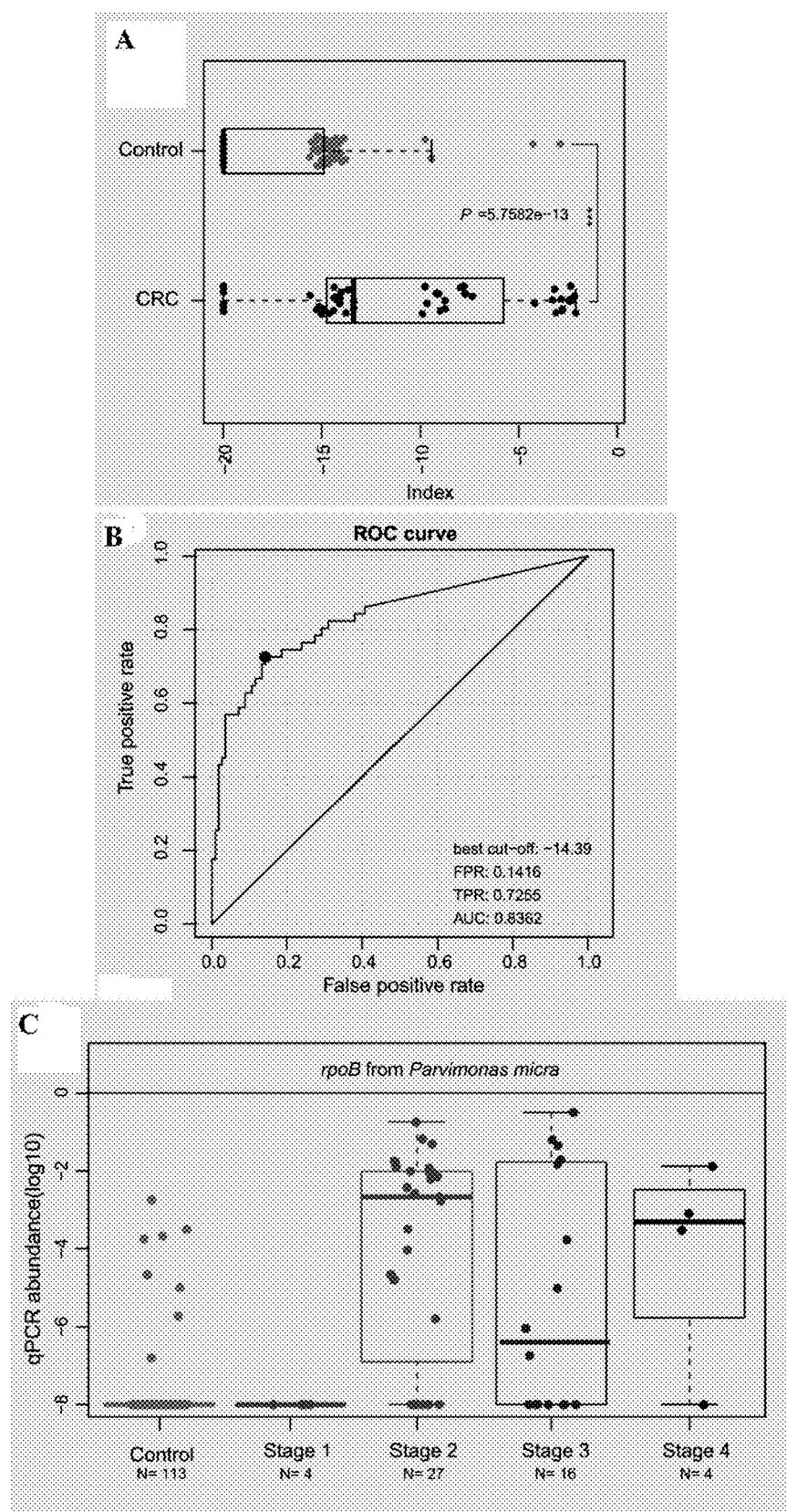

FIG. 8 shows the Receive-Operator-Curve of the CRC-specific species marker selection using the random forest method and three different species annotation methods: (A) the IMG species annotation method was carried out using clean reads to IMG version 400; (B) the mOTU species annotation method was carried out using published methods; and (C) all significant genes were clustered using MLG methods and species annotations using IMG version 400; and best cut-off are 0.445, 0.5604 and 0.6165 respectively; if probability of CRC is greater than the best cut-off, the subject has CRC or is at the risk of developing CRC;

FIG. 9 shows the stage-specific abundance of three species that are enriched in stage II and later, using three species annotation methods: MLG, IMG and mOTU;

FIG. 10 shows the species involved in gut microbial dysbiosis during colorectal cancer: the relative abundances of one bacterial species enriched in control microbiomes and three bacterial species enriched in CRC-associated microbiomes, during different stages of CRC (three different species annotation methods were used) are shown;

FIG. 11 shows the correlation between quantification by the metagenomic approach and quantitative polymerase chain reaction (qPCR) for two gene markers;

FIG. 12 shows the evaluation of the CRC index from 2 genes in Chinese cohort II: (A) the CRC index based on 2 gene markers separates CRC and control microbiomes; (B) ROC analysis reveals marginal potential for classification using the CRC index, with an area under the curve of 0.73; and FIG. 13 shows the validation of robust gene markers associated with CRC: qPCR abundance (in log 10 scale, zero abundance plotted as −8) of three gene markers was measured in cohort II, which consisted of 51 cases and 113 healthy controls; two gene markers were randomly selected (m1704941: butyryl-CoA dehydrogenase from *F. nucleatum*, m482585: RNA-directed DNA polymerase from an unknown microbe), and one was targeted (m1696299: RNA polymerase subunit beta, rpoB, from *P. micra*): (A) the CRC index based on the three genes clearly separates CRC microbiomes from controls; (B) the CRC index classifies has an area under the receiver operating characteristic (ROC) curve of 0.84; and (C) the *P. micra* species-specific rpoB gene shows relatively higher incidence and abundance starting in CRC stages II and III (P=2.15×10$^{-15}$) as compared to the control and stage I microbiomes.

DETAILED DESCRIPTION

Various publications, articles and patents are cited or described in the background and throughout the specification, each of these references is herein incorporated by reference in its entirety. Discussion of documents, acts, materials, devices, articles or the like which have been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. Terms such as "a", "an" and "the" are not intended to refer to only a singular entity, but include the general class for which a specific example can be used for illustration. The terminology herein is used to describe specific embodiments of the invention, but its usage does not delimit the invention, except as outlined in the claims.

In one general aspect, the present invention relates to a gene marker set for predicting the risk of colorectal cancer (CRC) in a subject. The set comprising marker genes having the nucleotide sequences of SEQ ID NO: 10, SEQ ID NO: 14 and SEQ ID NO: 6, respectively.

In another general aspect, the present invention relates to a method of using marker genes in a gene marker set according to an embodiment of the present invention for predicting the risk of colorectal cancer (CRC) in a subject in need thereof. The method comprises:

1) determining the abundance information of each marker gene in the gene marker set from sample j of the subject; and 2) calculating an index of sample j using the following formula:

$$I_j = \frac{\sum_i \epsilon_N \log 10(A_{ij} + 10^{-20})}{|N|},$$

wherein $A_{ij}$ is the abundance information of marker gene i in sample j, wherein i refers to each of the marker genes in the gene marker set, N is a subset of all of abnormal-associated marker genes related to the colorectal cancer in the gene marker set,

|N| is the number of the biomarkers in the subset, preferably |N| is 3;

wherein an index greater than a cutoff value indicates that the subject has or is at risk of developing CRC.

In another general aspect, the present invention relates to a method of using marker genes in a gene marker set according to an embodiment of the present invention for preparing a kit for predicting the risk of colorectal cancer (CRC) in a subject in need thereof. The method comprises:

1) determining the abundance information of each marker gene in the gene marker set from sample j of the subject; and 2) calculating an index of sample j using the following formula:

$$I_j = \frac{\sum_i \epsilon_N \log 10(A_{ij} + 10^{-20})}{|N|},$$

wherein $A_{ij}$ is the abundance information of marker gene i in sample j, wherein i refers to each of the marker genes in the gene marker set, N is a subset of all of abnormal-associated marker genes related to the colorectal cancer in the gene marker set, and

|N| is the number of the biomarkers in the subset, preferably |N| is 3;

wherein an index greater than a cutoff value indicates that the subject has or is at the risk of developing colorectal cancer (CRC).

In another general aspect, the present invention relates to a method of diagnosing whether a subject has colorectal cancer or is at the risk of developing colorectal cancer, comprising:

1) determining the abundance information of each of the marker genes comprising the nucleotide sequences of SEQ ID NO: 10, SEQ ID NO: 14 and SEQ ID NO:6, respectively, from sample j of the subject; and 2) calculating an index of sample j using the following formula:

$$I_j = \frac{\sum_i \epsilon_N \log 10(A_{ij} + 10^{-20})}{|N|},$$

wherein $A_{ij}$ is the abundance information of marker gene i in sample j, wherein i refers to each of the marker genes in the gene marker set, N is a subset of all of the CRC-associated marker genes, wherein the subset of CRC-associated marker genes comprising genes having the nucleotide sequences of SEQ ID NO: 10, SEQ ID NO: 14 and SEQ ID NO:6, respectively, and

|N| is the number of the marker genes in the subset, wherein |N| is 3, wherein an index greater than a cutoff value indicates that the subject has or is at the risk of developing colorectal cancer.

In one embodiment, the method further comprises collecting sample j from the subject and extracting DNA from the sample, prior to determining the abundance information of each of the gene markers in sample j.

In another embodiment, the abundance information is the relative abundance of each marker gene in a gene marker set, wherein the abundance information is determined based on the DNA level of the gene marker, for example, using a sequencing method.

In another embodiment, the abundance information is the relative abundance of each marker gene in a gene marker set, wherein the abundance information is determined using a qPCR method.

In another embodiment, the cutoff value is obtained by a Receiver Operator Characteristic (ROC) method, wherein the cutoff value corresponds to the value when the AUC (Area Under the Curve) is at its maximum.

In one preferred embodiment, the cutoff value is −14.39.

In another general aspect, the present invention provides a kit for analyzing a gene marker set according to an embodiment of the present invention. The kit comprises one or more oligonucleotides, such as primers and probes, that are configured to hybridize specifically to one or more marker genes within the gene marker set, including but not limited to those as set forth in Table 15, e.g., one or more sequences of SEQ ID NOs: 32-40. In some embodiments one or more detectable labels can be incorporated into an oligonucleotide at a 5' end, at a 3' end, and/or at any nucleotide position within the oligonucleotide.

In another general aspect, the present invention provides a method of using a marker gene comprising the nucleotide sequence of SEQ ID NO: 6, or of the rpoB gene encoding RNA polymerase subunit β, as a gene marker for predicting the risk of colorectal cancer (CRC) in a subject, wherein the enrichment of said marker gene in a sample from the subject relative to a sample from a control is indicative of a risk of colorectal cancer in the subject. For example, to determine whether the marker gene is enriched in a sample from the subject, the abundance information of the marker gene in the sample is compared with that from the control sample. If P<0.05, the marker gene is considered significantly different from that in the control. See, for example, FIG. 13C, $P=2.15\times10^{-15}$. Alternatively, as shown in FIG. 13C, the species' median of qPCR abundance is $10^{-2}$ to $10^{-7}$, a value range that can also be used for determining whether the marker gene is enriched in the sample. If the subject has a qPCR abundance greater than $10^{-7}$, the subject has CRC or is at the risk of developing CRC.

According to an embodiment of the invention, the method further comprises using at least one additional marker gene, such as the marker gene comprising the nucleotide sequence of SEQ ID NO: 10 or SEQ ID NO:14, for predicting the risk of CRC in a subject, wherein the enrichment of the additional marker gene in a sample from the subject relative to a sample from a control is further indicative of a risk of colorectal cancer in the subject.

Figure 6:
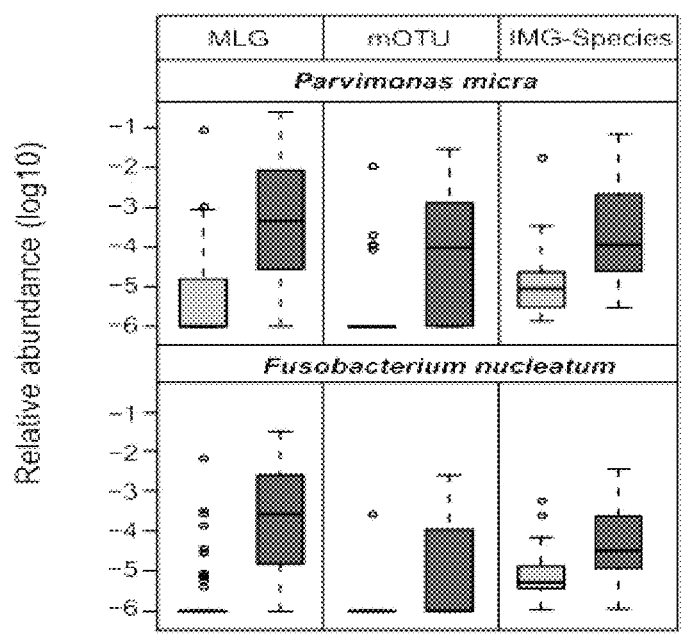
FIG. 6 shows species involved in gut microbial dysbiosis during colorectal cancer: the differential relative abundance of two CRC-associated and one control-associated microbial species were consistently identified using three different methods: MLG mOTU and the IMG database.

In another general aspect, the present invention provides a method of using *Parvimonas micra* as a species marker for predicting the risk of colorectal cancer (CRC) in a subject, wherein the enrichment of the species marker in a sample from the subject relative to a sample from a control is indicative of a risk of colorectal cancer in the subject. For example, to determine whether the species marker is enriched in a sample from the subject, the relative abundance of *Parvimonas micra* in the sample is compared with that from the control sample (see e.g., FIG. 6). If q<0.05 (also expressed as P<0.05, see Table 13), the species is considered significantly different, and it is enriched in CRC cohort. Alternatively, as shown in FIG. 6, the species' median of relative abundance is $10^{-3}$ to $10^{-5}$, a value range that can also be used for determining whether the marker species is enriched in the sample, e.g., if the subject has a relative abundance greater than $10^{-5}$, the subject has CRC or is at the risk of developing CRC.

The present invention is further exemplified in the following non-limiting Examples. Unless otherwise stated, parts and percentages are by weight and degrees are in Celsius. As is apparent to one of ordinary skill in the art, these Examples, while indicating preferred embodiments of the invention, are given by way of illustration only, and the agents referenced are all commercially available.

General Method

I. Methods for Detecting Biomarkers (Detect Biomarkers by Using MGWAS Strategy)

To define CRC-associated metagenomic markers, the inventors carried out a MGWAS (metagenome-wide association study) strategy (Qin et al., 2012, "A metagenome-wide association study of gut microbiota in type 2 diabetes," *Nature* 490, 55-60, incorporated herein by reference). Using a sequence-based profiling method, the inventors quantified the gut microbiota in samples. On average, with the requirement that there should be ≥90% identity, the inventors could uniquely map paired-end reads to the updated gene catalog. To normalize the sequencing coverage, the inventors used relative abundance instead of the raw read count to quantify the gut microbial genes. However, unlike what is done in a GWAS subpopulation correction, the inventors applied this analysis to microbial abundance rather than to genotype. A Wilcoxon rank-sum test was done on the adjusted gene profile to identify differential metagenomic gene contents between the CRC patients and controls. The outcome of the analyses showed a substantial enrichment of a set of microbial genes that had very small P values, as compared with the expected distribution under the null hypothesis, suggesting that these genes were true CRC-associated gut microbial genes.

The inventors next controlled the false discovery rate (FDR) in the analysis, and defined CRC-associated gene markers from these genes corresponding to a FDR.

II. Methods for Selecting the 31 Best Markers from the Biomarkers (Maximum Relevance Minimum Redundancy (mRMR) Feature Selection Framework)

To identify an optimal gene set, a minimum redundancy–maximum relevance (mRMR) (for detailed information, see Peng et al., 2005, "Feature selection based on mutual information: criteria of max-dependency, max-relevance, and min-redundancy," *IEEE Trans Pattern Anal Mach Intell.*, 27, 1226-1238, doi:10.1109/TPAMI.2005.159, which is incorporated herein by reference) feature selection method was used to select from all the CRC-associated gene markers. The inventors used the "sideChannelAttack" package of R software to perform the incremental search and found 128 sequential markers sets. For each sequential set, the inventors estimated the error rate by a leave-one-out cross-validation (LOOCV) of the linear discrimination classifier. The optimal selection of marker sets was the one corresponding to the lowest error rate. In the present study, the inventors made the feature selection on a set of 140,455 CRC-associated gene markers. Since it was computationally prohibitive to perform mRMR using all of the genes, the inventors derived a statistically non-redundant gene set. Firstly, the inventors pre-grouped the 140,455 colorectal cancer associated genes that were highly correlated with each other (Kendall correlation >0.9). Then the inventors chose the longest gene of each group as a representative gene for the group, since longer genes have a higher chance of being functionally annotated and will draw more reads during the mapping procedure. This generated a non-redundant set of 15,836 significant genes. Subsequently, the inventors applied the mRMR feature selection method to the 15,836 significant genes and identified an optimal set of 31 gene biomarkers that are strongly associated with colorectal cancer for colorectal cancer classification, which are shown in Table 1. The gene id is from the published reference gene catalog as Qin et al. 2012, supra.

TABLE 1

31 optimal Gene markers' enrichment information

| Gene id | Correlation coefficient with CRC | mRMR rank | Enrichment (1 = Control, 0 = CRC) | SEQ ID NO: |
|---|---|---|---|---|
| 2361423 | −0.558205377 | 1 | 0 | 1 |
| 2040133 | −0.500237832 | 2 | 0 | 2 |
| 3246804 | −0.454281109 | 3 | 0 | 3 |
| 3319526 | 0.441366585 | 4 | 1 | 4 |
| 3976414 | 0.431923463 | 5 | 1 | 5 |
| 1696299 | −0.499397182 | 6 | 0 | 6 |
| 2211919 | 0.410506085 | 7 | 1 | 7 |
| 1804565 | 0.418663439 | 8 | 1 | 8 |
| 3173495 | −0.55118428 | 9 | 0 | 9 |
| 482585 | −0.454270958 | 10 | 0 | 10 |
| 181682 | 0.400814213 | 11 | 1 | 11 |
| 3531210 | 0.383705453 | 12 | 1 | 12 |
| 3611706 | 0.413879567 | 13 | 1 | 13 |
| 1704941 | −0.468122499 | 14 | 0 | 14 |
| 4256106 | 0.42048024 | 15 | 1 | 15 |
| 4171064 | 0.43365554 | 16 | 1 | 16 |
| 2736705 | −0.417069104 | 17 | 0 | 17 |
| 2206475 | 0.411512652 | 18 | 1 | 18 |
| 370640 | 0.399015232 | 19 | 1 | 19 |
| 1559769 | 0.427134509 | 20 | 1 | 20 |
| 3494506 | 0.382302723 | 21 | 1 | 21 |
| 1225574 | −0.407066113 | 22 | 0 | 22 |
| 1694820 | −0.442595115 | 23 | 0 | 23 |
| 4165909 | 0.410519669 | 24 | 1 | 24 |

TABLE 1-continued 31 optimal Gene markers' enrichment information

| Gene id | Correlation coefficient with CRC | mRMR rank | Enrichment (1 = Control, 0 = CRC) | SEQ ID NO: |
|---|---|---|---|---|
| 3546943 | −0.395361093 | 25 | 0 | 25 |
| 3319172 | 0.448526551 | 26 | 1 | 26 |
| 1699104 | −0.467388978 | 27 | 0 | 27 |
| 3399273 | 0.388569946 | 28 | 1 | 28 |
| 3840474 | 0.383705453 | 29 | 1 | 29 |
| 4148945 | 0.407802676 | 30 | 1 | 30 |
| 2748108 | −0.426515966 | 31 | 0 | 31 |

III. Gut Healthy Index (CRC Index)

To exploit the potential ability of disease classification by gut microbiota, the inventors developed a disease classifier system based on the gene markers that the inventors defined. For intuitive evaluation of the risk of disease based on these gut microbial gene markers, the inventors calculated a gut healthy index (CRC index).

To evaluate the effect of the gut metagenome on CRC, the inventors defined and calculated the gut healthy index for each individual on the basis of the selected 31 gut metagenomic marker genes as described above. For each individual sample, the gut healthy index of sample j, denoted by $I_j$ was calculated by the formula below:

$$I_j = \left[ \frac{\sum_i \epsilon_N \log10(A_{ij} + 10^{-20})}{|N|} - \frac{\sum_i \epsilon_M \log10(A_{ij} + 10^{-20})}{|M|} \right],$$

wherein $A_{ij}$ is the relative abundance of marker i in sample j,

N is a subset of all of the patient-enriched markers in selected biomarkers related to the abnormal condition (e.g., a subset of all of the CRC-associated marker genes in these 31 selected gut metagenomic markers), M is a subset of all of the control-enriched markers in the selected biomarkers related to the abnormal condition (e.g., a subset of all control-associated marker genes in these 31 selected gut metagenomic markers), and

|N| and |M| are the numbers (sizes) of the biomarkers in these two sets, respectively.

IV. Receiver Operator Characteristic (ROC) Analysis

The inventors applied the ROC analysis to assess the performance of the colorectal cancer classification based on metagenomic markers. Based on the 31 gut metagenomic markers selected above, the inventors calculated the CRC index for each sample. The inventors then used the "Daim" package of R software to draw the ROC curve.

V. Disease Classifier System

After identifying biomarkers using the MGWAS strategy and the rule that the biomarkers used should yield the highest classification between disease and healthy samples with the least redundancy, the inventors ranked the biomarkers by a minimum redundancy–maximum relevance (mRMR) and found sequential markers sets (the size can be as large as the number of biomarkers). For each sequential set, the inventors estimated the error rate using a leave-one-out cross-validation (LOOCV) of a classifier. The optimal selection of marker sets corresponded to the lowest error rate (In some embodiments, the inventors have selected 31 biomarkers).

Finally, for intuitive evaluation of the risk of disease based on these gut microbial gene markers, the inventors calculated a gut healthy index. The larger the healthy index, the higher the risk of disease. The smaller the healthy index, the more healthy the subjects. The inventors can build an optimal healthy index cutoff using a large cohort. If the healthy index of the test sample is larger than the cutoff, then the subject is at a higher disease risk. If the healthy index of the test sample is smaller than the cutoff, then the subject has a low risk of disease. The optimal healthy index cutoff can be determined using a ROC method when the AUC (Area Under the Curve) is at its maximum.

EXAMPLE 1

Identifying 31 Biomarkers from 128 Chinese Individuals and Using a Gut Healthy Index to Evaluate their Colorectal Cancer Risk 1.1 Sample Collection and DNA Extraction Stool samples from 128 subjects (cohort I), including 74 colorectal cancer patients and 54 healthy controls (Table 2) were collected in the Prince of Wales Hospital, Hong Kong with informed consent. To be eligible for inclusion in this study, individuals had to fit the following criteria for stool sample collection: 1) no taking of antibiotics or other medications, no special diets (diabetics, vegetarians, etc), and having a normal lifestyle (without extra stress) for a minimum of 3 months; 2) a minimum of 3 months after any medical intervention; 3) no history of colorectal surgery, any kind of cancer, or inflammatory or infectious diseases of the intestine. Subjects were asked to collect stool samples before a colonoscopy examination in standardized containers at home and store the samples in their home freezer immediately. Frozen samples were then delivered to the Prince of Wales Hospital in insulating polystyrene foam containers and stored at −80° C. immediately until use.

Stool samples were thawed on ice and DNA extraction was performed using the QiagenQIAamp DNA Stool Mini Kit according to the manufacturer's instructions. Extracts were treated with DNase-free RNase to eliminate RNA contamination. DNA quantity was determined using a Nano-Drop spectrophotometer, a Qubit Fluorometer (with the Quant-iTTMdsDNA BR Assay Kit) and gel electrophoresis.

TABLE 2

Baseline characteristics of colorectal cancer cases and controls in cohort I. BMI: body mass index; eGFR: epidermal growth factor receptor; DM: diabetes mellitus type 2.

| Parameter | Controls (n = 54) | Cases (n = 74) |
|---|---|---|
| Age | 61.76 | 66.04 |
| Sex (M:F) | 33:21 | 48:26 |
| BMI | 23.47 | 23.9 |
| eGFR | 72.24 | 74.15 |
| DM (%) | 16 (29.6%) | 29 (39.2%) |
| Enterotype (1:2:3) | 26:22:6 | 37:31:6 |
| Stage of disease (1:2:3:4) | n.a. | 16:21:30:7 |
| Location (proximal:distal) | n.a. | 13:61 |

1.2 DNA Library Construction and Sequencing

DNA library construction was performed following the manufacturer's instruction (Illumina HiSeq 2000 platform). The inventors used the same workflow as described previously to perform cluster generation, template hybridization, isothermal amplification, linearization, blocking and denaturation, and hybridization of the sequencing primers (Qin, J. et al. (2012), "A metagenome-wide association study of gut microbiota in type 2 diabetes," Nature, 490, 55-60, incorporated herein by reference).

The inventors constructed one paired-end (PE) library with an insert size of 350 bp for each sample, followed by high-throughput sequencing to obtain around 30 million PE reads of a length of 2×100 bp. High quality reads were extracted by filtering out low quality reads containing 'N's in the read, filtering out adapter contamination and human DNA contamination from the raw data, and trimming low quality terminal bases of reads. 751 million metagenomic reads (high quality reads) were generated (5.86 million reads per individual on average, Table 3).

1.3 Reads Mapping

The inventors mapped the high quality reads (Table 3) to a published reference gut gene catalog established from European and Chinese adults (Qin, J. et al. (2012), "A metagenome-wide association study of gut microbiota in type 2 diabetes," Nature, 490, 55-60, incorporated herein by reference) (identity>=90%), and the inventors then derived the gene profiles using the same method of Qin et al. 2012, supra. From the reference gene catalog as Qin et al. 2012, supra, the inventors derived a subset of 2,110,489 (2.1M) genes that appeared in at least 6 of the 128 samples.

1.4 Analysis of Factors Influencing Gut Microbiota Gene Profiles

To ensure robust comparison of the gene content of the 128 metagenomes, the inventors generated a set of 2,110,489 (2.1M) genes that were present in at least 6 subjects, and generated 128 gene abundance profiles using these 2.1 million genes. The inventors used the permutational multivariate analysis of variance (PERMANOVA) test to assess the effect of different characteristics, including age, BMI, eGFR, TCHO, LDL, HDL, TG, gender, DM, CRC status, smoking status and location, on the gene profiles of the 2.1M genes. The inventors performed the analysis using the "vegan" function of R, and the permuted p-value was obtained after 10,000 permutations. The inventors also corrected for multiple testing using the "p.adjust" function of R with the Benjamini-Hochberg method to get the q-value for each gene.

When the inventors performed permutational multivariate analysis of variance (PERMANOVA) on 13 different covariates, only a CRC status was significantly associated with these gene profiles (q=0.0028, Table 4), showing a stronger association than the second-best determinant, body mass index (q=0.15). Thus, the data suggest an altered gene composition in CRC patient microbiomes.

TABLE 4

PERMANOVA analysis using the microbial gene profile. Analysis was conducted to test whether clinical parameters and colorectal cancer (CRC) status have a significant impact on the gut microbiota with q < 0.05.

| Phenotype | Df | SumsOfSqs | MeanSqs | F.Model | R2 | Pr (>F) | q-value |
|---|---|---|---|---|---|---|---|
| CRC Status | 1 | 0.679293 | 0.679293 | 1.95963 | 0.015314 | 0.0004 | 0.0028 |
| BMI | 1 | 0.484289 | 0.484289 | 1.39269 | 0.011019 | 0.033 | 0.154 |
| DM Status | 1 | 0.438359 | 0.438359 | 1.257642 | 0.009883 | 0.084 | 0.27272 |
| Location | 1 | 0.436417 | 0.436417 | 1.228172 | 0.016772 | 0.0974 | 0.27272 |
| Age | 1 | 0.397282 | 0.397282 | 1.138728 | 0.008957 | 0.1923 | 0.4487 |
| HDL | 1 | 0.38049 | 0.38049 | 1.083265 | 0.010509 | 0.271 | 0.542 |
| TG | 1 | 0.365191 | 0.365191 | 1.039593 | 0.010089 | 0.3517 | 0.564964 |
| eGFR | 1 | 0.358527 | 0.358527 | 1.023138 | 0.009471 | 0.38 | 0.564964 |
| CRC Stage | 1 | 0.357298 | 0.357298 | 1.002413 | 0.013731 | 0.441 | 0.564964 |
| Smoker | 1 | 0.347969 | 0.347969 | 0.999825 | 0.013511 | 0.4439 | 0.564964 |
| TCHO | 1 | 0.321989 | 0.321989 | 0.915216 | 0.008893 | 0.6539 | 0.762883 |
| LDL | 1 | 0.306483 | 0.306483 | 0.871306 | 0.00847 | 0.7564 | 0.814585 |
| Gender | 1 | 0.267738 | 0.267738 | 0.765162 | 0.006036 | 0.9528 | 0.9528 |

BMI: body mass index;
DM: diabetes mellitus type 2;
HDL: high density lipoprotein;
TG: triglyceride;
eGFR: epidermal growth factor receptor;
TCHO: total cholesterol;
LDL; low density lipoprotein.

TABLE 3

Summary of metagenomic data and mapping to reference gene catalog. The fourth column reports P-value results from Wilcoxon rank-sum tests.

| Parameter | Controls | Cases | P-value |
|---|---|---|---|
| Average raw reads | 60162577 | 60496561 | 0.8082 |
| After removing low quality reads | 59423292 (98.77%) | 59715967 (98.71%) | 0.831 |
| After removing human reads | 59380535 ± 7378751 | 58112890 ± 10324458 | 0.419 |
| Mapping rate | 66.82% | 66.27% | 0.252 |

Figure 1:
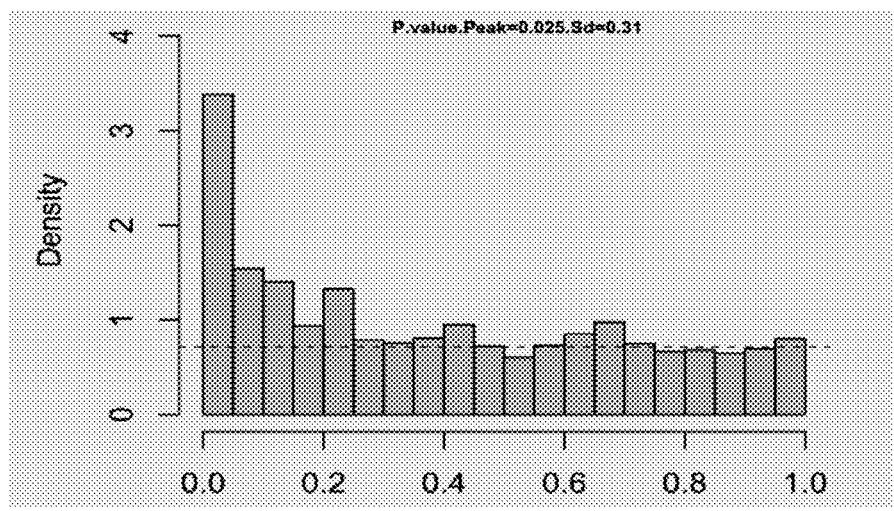

1.5 CRC-associated Genes Identified by MGWAS 1.5.1 Identification of colorectal cancer associated genes. The inventors performed a metagenome wide association study (MGWAS) to identify the genes contributing to the altered gene composition in the CRC samples. To identify the association between the metagenomic profile and colorectal cancer, a two-tailed Wilcoxon rank-sum test was used in the 2.1M (2,110,489) gene profiles. The inventors identified 140,455 gene markers, which were enriched in either case or control samples with P<0.01 (FIG. 1).

1.5.2 Estimating the false discovery rate (FDR). Instead of a sequential P-value rejection method, the inventors applied the "qvalue" method proposed in a previous study (J. D. Storey and R. Tibshirani (2003), "Statistical significance for genomewide studies," Proceedings of the National Academy of Sciences of the United States of America, 100, 9440, incorporated herein by reference) to estimate the FDR. In the MGWAS, the statistical hypothesis tests were performed on a large number of features of the 140,455 genes. The false discovery rate (FDR) was 11.03%.

1.6 Gut Microbiota-Based CRC Classification

Figure 2:
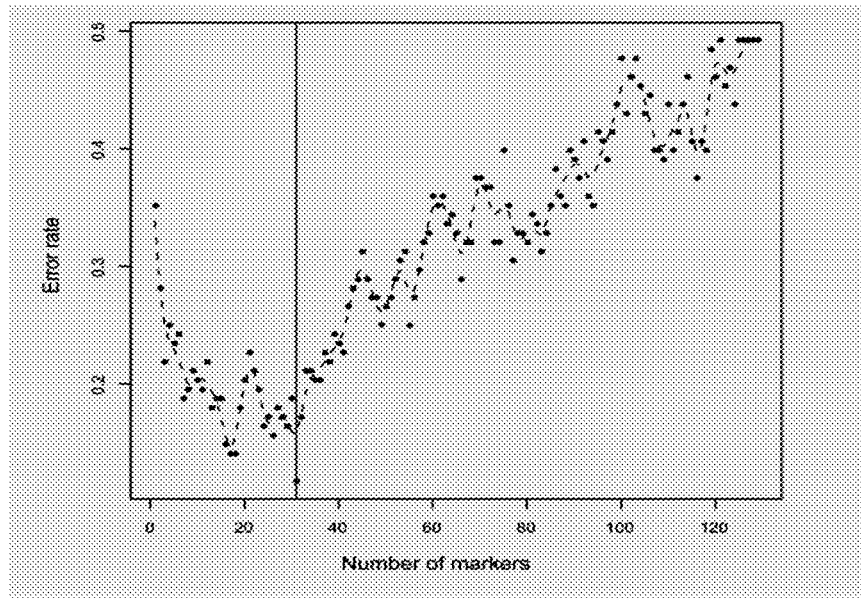
Figure 3:
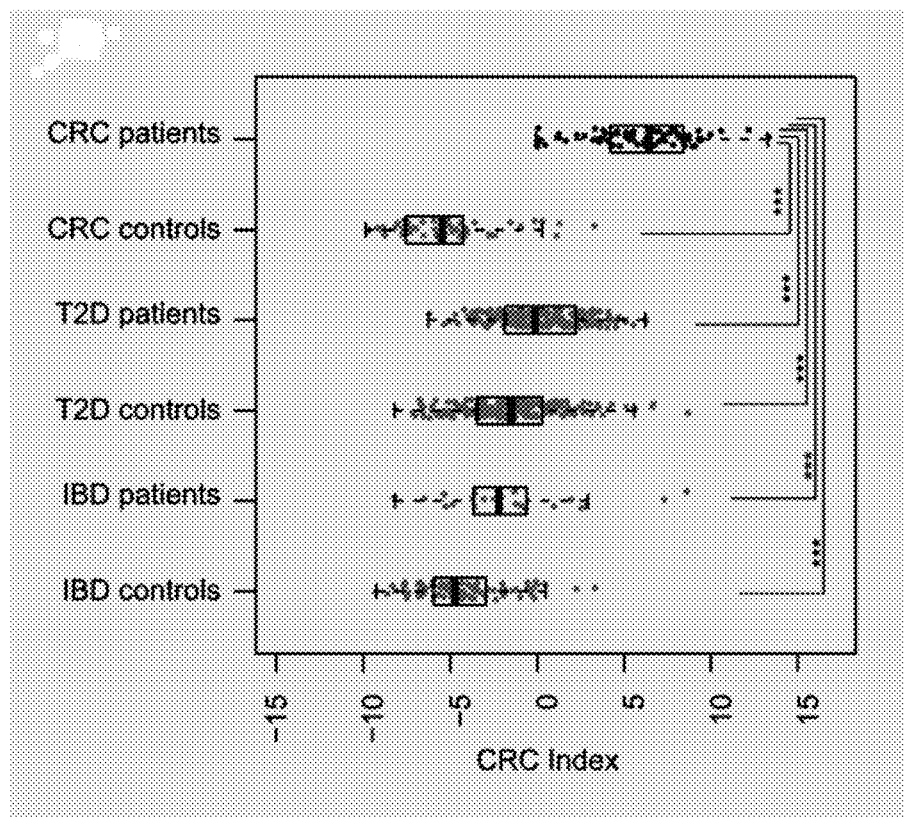
Figure 4:
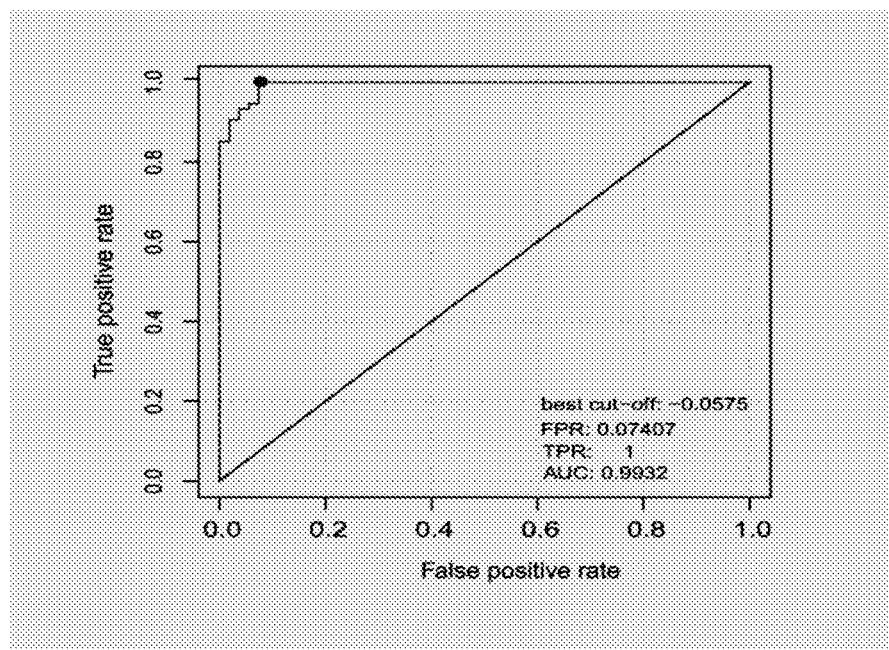

The inventors proceeded to identify potential biomarkers for CRC from the genes associated with the disease, using the minimum redundancy maximum relevance (mRMR) feature selection method. However, since the computational complexity of this method did not allow them to use all 140,455 genes from the MGWAS approach, the inventors had to reduce the number of candidate genes. First, the inventors selected a stricter set of 36,872 genes with higher statistical significance (P<0.001; FDR=4.147%). Then the inventors identified groups of genes that were highly correlated with each other (Kendall's τ>0.9) and chose the longest gene in each group, generating a statistically non-redundant set of 15,836 significant genes. Finally, the inventors used the mRMR method and identified an optimal set of 31 genes that were strongly associated with CRC status (FIG. 2, Table 5). The inventors computed a CRC index based on the relative abundance of these markers, which clearly separated the CRC patient microbiomes from the control microbiomes (Table 6), as well as from 490 fecal microbiomes from two previous studies on type 2 diabetes in Chinese individuals (Qin et al. 2012, supra) and inflammatory bowel disease in European individuals (J. Qin et al., 2010, "A human gut microbial gene catalogue established by metagenomic sequencing," *Nature*, 464, 59, incorporated herein by reference) (FIG. 3, the median CRC-indexes for patients and controls in this study were 6.42 and −5.48, respectively; Wilcoxon rank-sum test, $q<2.38\times10^{-10}$ for all five comparisons, see Table 7). Classification of the 74 CRC patient microbiomes against the 54 control microbiomes using the CRC index exhibited an area under the receiver operating characteristic (ROC) curve of 0.9932 (FIG. 4). At the cutoff −0.0575, the true positive rate (TPR) was 1, and the false positive rate (FPR) was 0.07407, indicating that the 31 gene markers could be used to accurately classify CRC individuals.

TABLE 6

128 samples' calculated gut healthy index (CRC patients and non-CRC controls)

| Sample ID | Type (Con_CRC:non-CRC controls; CRC:CRC patients) | CRC-index | Sample ID | Type (Con_CRC:non-CRC controls; CRC:CRC patients) | CRC-index |
|---|---|---|---|---|---|
| 502A | Con_CRC | −7.505749695 | A10A | CRC | 13.26483131 |
| 512A | Con_CRC | −5.150023018 | M2.PK002A | CRC | 7.002094781 |
| 515A | Con_CRC | −4.919398163 | M2.PK003A | CRC | 5.108478224 |
| 516A | Con_CRC | −2.793151285 | M2.PK018A | CRC | 2.243592264 |
| 517A | Con_CRC | −8.078128133 | M2.PK019A | CRC | −0.057498133 |
| 519A | Con_CRC | −7.556675412 | M2.PK021A | CRC | 7.878402029 |
| 530A | Con_CRC | −0.194519906 | M2.PK022A | CRC | 9.047909247 |
| 534A | Con_CRC | −5.251127609 | M2.PK023A | CRC | 5.428574192 |
| 536A | Con_CRC | −7.08635459 | M2.PK024A | CRC | 5.032760805 |
| M2.PK504A | Con_CRC | −5.470747464 | M2.PK026A | CRC | 6.257085759 |
| M2.PK514A | Con_CRC | −4.441183208 | M2.PK027A | CRC | 1.59430903 |
| M2.PK520B | Con_CRC | −8.101427301 | M2.PK029A | CRC | 9.331138747 |
| M2.PK522A | Con_CRC | 0.269338093 | M2.PK030A | CRC | 4.728023967 |
| M2.PK523A | Con_CRC | −6.980913756 | M2.PK032A | CRC | 6.055831256 |
| M2.PK524A | Con_CRC | −9.027027667 | M2.PK037A | CRC | 4.227424374 |
| M2.PK531B | Con_CRC | −5.483143199 | M2.PK038A | CRC | 2.669264211 |
| M2.PK532A | Con_CRC | −5.96003222 | M2.PK041A | CRC | 4.558926807 |
| M2.PK533A | Con_CRC | −7.718764145 | M2.PK042A | CRC | 3.47308125 |
| M2.PK543A | Con_CRC | −9.844975269 | M2.PK043A | CRC | 5.347387703 |
| M2.PK548A | Con_CRC | −4.062846751 | M2.PK045A | CRC | 8.09166979 |
| M2.PK556A | Con_CRC | −4.15150788 | M2.PK046A | CRC | 9.235279951 |
| M2.PK558A | Con_CRC | −9.712104855 | M2.PK047A | CRC | 8.45229555 |
| M2.PK602A | Con_CRC | −7.380042553 | M2.PK051A | CRC | 6.602608047 |
| M2.PK615A | Con_CRC | 3.232971256 | M2.PK052A | CRC | 3.207800397 |
| M2.PK617A | Con_CRC | −8.878473599 | M2.PK055A | CRC | 5.088317256 |
| M2.PK619A | Con_CRC | −8.279540689 | M2.PK056B | CRC | 5.504229632 |
| M2.PK630A | Con_CRC | −5.993197547 | M2.PK059A | CRC | 5.466091636 |
| M2.PK644A | Con_CRC | 1.230424198 | M2.PK063A | CRC | 3.758294225 |
| M2.PK647A | Con_CRC | −7.181191393 | M2.PK064A | CRC | 3.763414393 |
| M2.PK649A | Con_CRC | −1.576643721 | M2.PK065A | CRC | 6.486959786 |
| M2.PK653A | Con_CRC | −4.246899704 | M2.PK066A | CRC | 1.199091901 |
| M2.PK656A | Con_CRC | −5.80900221 | M2.PK067A | CRC | 9.938025463 |
| M2.PK659A | Con_CRC | −7.805935646 | M2.PK069B | CRC | −0.04402983 |
| M2.PK663A | Con_CRC | −5.007057718 | M2.PK083B | CRC | 8.394697958 |
| M2.PK699A | Con_CRC | −8.827532431 | M2.PK084A | CRC | 9.25322799 |
| M2.PK701A | Con_CRC | −0.981728615 | M2.PK085A | CRC | 7.852591304 |
| M2.PK705A | Con_CRC | −8.822384737 | MSC103A | CRC | 4.05476664 |
| M2.PK708A | Con_CRC | −6.573782359 | MSC119A | CRC | 4.331580986 |

TABLE 6-continued 128 samples' calculated gut healthy index (CRC patients and non-CRC controls)

| Sample ID | Type (Con_CRC:non-CRC controls; CRC:CRC patients) | CRC-index | Sample ID | Type (Con_CRC:non-CRC controls; CRC:CRC patients) | CRC-index |
|---|---|---|---|---|---|
| M2.PK710A | Con_CRC | −7.558945558 | MSC120A | CRC | 3.865826479 |
| M2.PK712A | Con_CRC | −9.207916748 | MSC1A | CRC | 9.930238103 |
| M2.PK723A | Con_CRC | −4.481542621 | MSC45A | CRC | 9.331894011 |
| M2.PK725A | Con_CRC | −7.520375154 | MSC4A | CRC | 0.006971195 |
| M2.PK729A | Con_CRC | −5.318926226 | MSC54A | CRC | 12.10968629 |
| M2.PK730A | Con_CRC | −4.3710193 | MSC5A | CRC | 3.272778932 |
| M2.PK732A | Con_CRC | −5.20132309 | MSC63A | CRC | 7.74197911 |
| M2.PK750A | Con_CRC | −6.64771202 | MSC6A | CRC | 8.063701275 |
| M2.PK751A | Con_CRC | −3.65391467 | MSC76A | CRC | 6.730976418 |
| M2.PK797A | Con_CRC | −4.675123647 | MSC78A | CRC | 6.999247399 |
| M2.PK801A | Con_CRC | −7.766321018 | MSC79A | CRC | 6.805539524 |
| 509A | Con_CRC | −2.479402638 | MSC81A | CRC | 8.465000094 |
| A60A | Con_CRC | 1.078322254 | M118A | CRC | 8.675933723 |
| 506A | Con_CRC | −4.246837899 | M123A | CRC | 8.627635602 |
| A21A | Con_CRC | −4.440375851 | M2.Pk.001A | CRC | 7.78045553 |
| A51A | Con_CRC | −2.809587066 | M2.Pk.005A | CRC | 4.534189338 |
| | | | M2.Pk.009A | CRC | 8.188718934 |
| | | | M2.Pk.017A | CRC | 6.225010462 |
| | | | M84A | CRC | 3.497922009 |
| | | | M89A | CRC | 0.394210537 |
| | | | M2.Pk.007A | CRC | 5.703428174 |
| | | | M2.Pk.010A | CRC | 7.231959163 |
| | | | M122A | CRC | 8.387516145 |
| | | | M2.Pk.004A | CRC | 4.246104721 |
| | | | M2.Pk.008A | CRC | 5.299578303 |
| | | | M2.Pk.011A | CRC | 6.354957821 |
| | | | M2.Pk.015A | CRC | 7.719629705 |
| | | | M113A | CRC | 7.528437656 |
| | | | M116A | CRC | 10.54991338 |
| | | | M117A | CRC | 0.072052278 |
| | | | M2.Pk.006A | CRC | 9.368358379 |
| | | | M2.Pk.012A | CRC | 1.112535148 |
| | | | M2.Pk.014A | CRC | 8.671786146 |
| | | | M2.Pk.016A | CRC | 8.898356611 |
| | | | M115A | CRC | 7.241420602 |
| | | | M2.Pk.013A | CRC | 7.331598086 |

EXAMPLE 2

Validating the 31 Biomarkers

The inventors validated the discriminatory power of the CRC classifier using another new independent study group, including 19 CRC patients and 16 non-CRC controls that were also collected in the Prince of Wales Hospital.

For each sample, DNA was extracted and a DNA library was constructed followed by high throughput sequencing as described in Example 1. The inventors calculated the gene abundance profile for these samples using the same method as described in Qin et al. 2012, supra. The relative abundance of each of the gene markers as set forth in SEQ ID NOs: 1-31 was then determined. The index of each sample was then calculated using the following formula:

$$I_j = \left[ \frac{\sum_i \epsilon_N \log 10(A_{ij} + 10^{-20})}{|N|} - \frac{\sum_i \epsilon_M \log 10(A_{ij} + 10^{-20})}{|M|} \right],$$

wherein:

$A_{ij}$ is the relative abundance of marker i in sample j, wherein i refers to each of the gene markers as set forth in SEQ ID NOs 1-31, N is a subset of all of the patient-enriched markers and M is a subset of all of the control-enriched markers, the subset of CRC-enriched markers and the subset of control-enriched markers are shown in Table 1, and

|N| and |M| are numbers (sizes) of the biomarkers in these two subsets, respectively, wherein |N| is 13 and |M| is 18.

Table 8 shows the calculated index of each sample and Table 9 shows the relevant gene relative abundance of a representative sample, V30.

Figure 5:
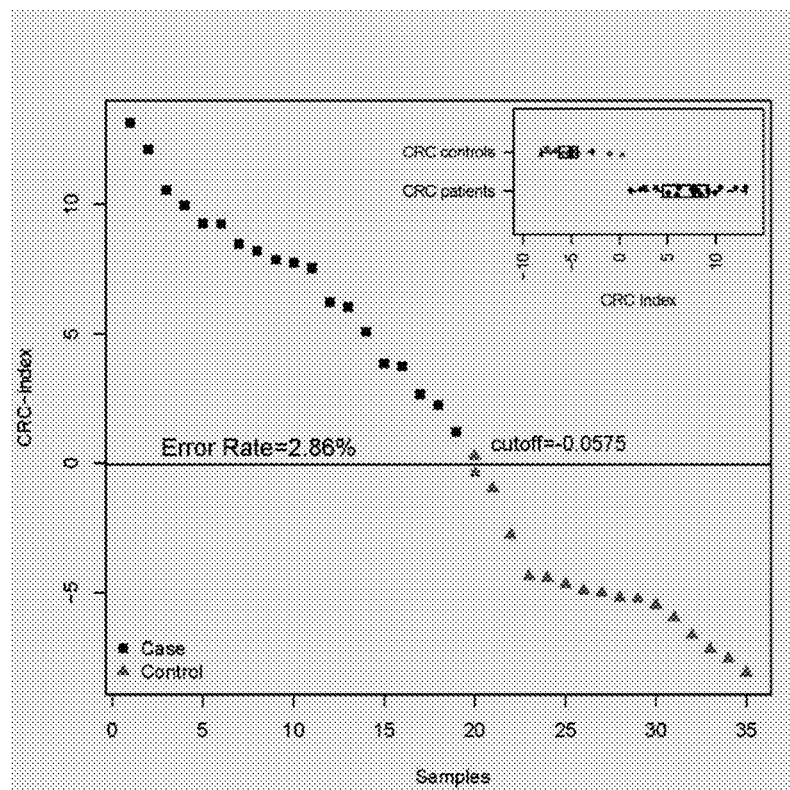

In this assessment analysis, the top 19 samples with the highest gut healthy index were all CRC patients, and all of the CRC patients were diagnosed as CRC individuals (Table 8 and FIG. 5) Only one of the non-CRC controls (FIG. 5,the triangle with *) was diagnosed as a CRC patient. At the cutoff −0.0575, the error rate was 2.86%, validating that the 31 gene markers can accurately classify CRC individuals.

TABLE 8

35 samples' calculated gut healthy index

| Sample ID | Type (Con_CRC:non-CRC controls; CRC:CRC patients) | CRC-index | Sample ID | Type (Con_CRC:non-CRC controls; CRC:CRC patients) | CRC-index |
|---|---|---|---|---|---|
| V27 | Con_CRC | 0.269338056 | V35 | CRC | 13.16483131 |
| V19 | Con_CRC | −0.981728643 | V8 | CRC | 12.12968629 |
| V26 | Con_CRC | −2.793151257 | V13 | CRC | 10.54991338 |
| V10 | Con_CRC | −4.371019 | V7 | CRC | 9.958035463 |
| V18 | Con_CRC | −4.440375832 | V17 | CRC | 9.2432279 |
| V1 | Con_CRC | −4.675123655 | V2 | CRC | 9.235252955 |
| V14 | Con_CRC | −4.919398178 | V15 | CRC | 8.465000028 |
| V9 | Con_CRC | −5.007057768 | V25 | CRC | 8.188718932 |
| V33 | Con_CRC | −5.20132324 | V20 | CRC | 7.852591353 |
| V29 | Con_CRC | −5.251127667 | V3 | CRC | 7.74197955 |
| V6 | Con_CRC | −5.470747485 | V24 | CRC | 7.528437632 |
| V21 | Con_CRC | −5.96003246 | V16 | CRC | 6.225010478 |
| V22 | Con_CRC | −6.64771297 | V30 | CRC | 6.055831257 |
| V23 | Con_CRC | −7.181191336 | V31 | CRC | 5.088317266 |
| V5 | Con_CRC | −7.558945528 | V28 | CRC | 3.865826489 |
| V32 | Con_CRC | −8.101427363 | V4 | CRC | 3.758294237 |
|  |  |  | V11 | CRC | 2.669264236 |
|  |  |  | V34 | CRC | 2.243592293 |
|  |  |  | V12 | CRC | 1.199091982 |

TABLE 9

Gene relative abundance of Sample V30

| Gene id | Enrichment (1 = Control, 0 = CRC) | SEQ ID NO: | Calculation of gene relative abundance |
|---|---|---|---|
| 2361423 | 0 | 1 | 2.24903E−05 |
| 2040133 | 0 | 2 | 8.77418E−08 |
| 3246804 | 0 | 3 | 0 |
| 3319526 | 1 | 4 | 0 |
| 3976414 | 1 | 5 | 0 |
| 1696299 | 0 | 6 | 4.04178E−06 |
| 2211919 | 1 | 7 | 7.89676E−07 |
| 1804565 | 1 | 8 | 0 |
| 3173495 | 0 | 9 | 0.000020166 |
| 482585 | 0 | 10 | 0 |
| 181682 | 1 | 11 | 0 |
| 3531210 | 1 | 12 | 0 |
| 3611706 | 1 | 13 | 0 |
| 1704941 | 0 | 14 | 1.73798E−06 |
| 4256106 | 1 | 15 | 0 |
| 4171064 | 1 | 16 | 9.35913E−08 |
| 2736705 | 0 | 17 | 1.41059E−07 |
| 2206475 | 1 | 18 | 3.12301E−07 |
| 370640 | 1 | 19 | 0 |
| 1559769 | 1 | 20 | 0 |
| 3494506 | 1 | 21 | 0 |
| 1225574 | 0 | 22 | 0 |
| 1694820 | 0 | 23 | 4.57783E−07 |
| 4165909 | 1 | 24 | 0 |
| 3546943 | 0 | 25 | 0 |
| 3319172 | 1 | 26 | 0 |
| 1699104 | 0 | 27 | 4.74411E−06 |
| 3399273 | 1 | 28 | 6.0661E−08 |
| 3840474 | 1 | 29 | 0 |
| 4148945 | 0 | 30 | 3.00829E−07 |
| 2748108 | 0 | 31 | 8.14399E−08 |

The inventors have therefore identified and validated a 31 markers set that was determined using a minimum redundancy–maximum relevance (mRMR) feature selection method based on 140,455 CRC-associated markers. The inventors have also developed a gut healthy index to evaluate the risk of CRC disease based on these 31 gut microbial gene markers.

EXAMPLE 3

Identifying Species Biomarkers from the 128 Chinese Individuals

Based on the sequencing reads of the 128 microbiomes from cohort 1 in Example 1, the inventors examined the taxonomic differences between control and CRC-associated microbiomes to identify microbial taxa contributing to the dysbiosis. For this, the inventors used taxonomic profiles derived from three different methods, as supporting evidence from multiple methods would strengthen an association. First, the inventors mapped metagenomic reads to 4650 microbial genomes in the IMG database (version 400) and estimated the abundance of microbial species included in that database (denoted IMG species). Second, the inventors estimated the abundance of species-level molecular operational taxonomic units (mOTUs) using universal phylogenetic marker genes. Third, the inventors organized the 140,455 genes identified by MGWAS into metagenomic linkage groups (MLGs) that represent clusters of genes originating from the same genome, and they annotated the MLGs at the species level using the IMG database whenever possible, grouped the MLGs based on these species annotations, and estimated the abundance of these species (denoted MLG species).

3.1 Species Annotation of IMG Genomes

For each IMG genome, using the NCBI taxonomy identifier provided by IMG, the inventors identified the corresponding NCBI taxonomic classification at the species and genus levels using NCBI taxonomy dump files. The genomes without corresponding NCBI species names were left with their original IMG names, most of which were unclassified.

3.2 Data Profile Construction 3.2.1 Gene Profiles

The inventors mapped their high-quality reads to a published reference gut gene catalog established from European and Chinese adults (identity>=90%), and the inventors then derived the gene profiles using the same method of Qin et al. 2012, supra.

3.2.2 mOTU Profile

Clean reads (high quality reads, as in Example 1) were aligned to the mOTU reference (79268 sequences total) with default parameters (S. Sunagawa et al. (2013), "Metagenomic species profiling using universal phylogenetic marker genes," *Nature methods*, 10, 1196, incorporated herein by reference). 549 species-level mOTUs were identified, including 307 annotated species and 242 mOTU linkage groups without representative genomes, the latter of which were putatively Firmicutes or Bacteroidetes.

3.2.3 IMG-species and IMG-genus Profiles

Bacterial, archaeal and fungal sequences were extracted from the IMG v400 reference database (V. M. Markowitz et al. (2012), "IMG: the Integrated Microbial Genomes database and comparative analysis system," *Nucleic acids research*, 40, D115, incorporated herein by reference) downloaded from http://ftp.jgi-psf.org. 522,093 sequences were obtained in total, and a SOAP reference index was constructed based on 7 equal-sized segments of the original file. Clean reads were aligned to the reference using a SOAP aligner (R. Li et al. (2009), "SOAP2: an improved ultrafast tool for short read alignment," *Bioinformatics*, 25, 1966, incorporated herein by reference) version 2.22, with the parameters "-m 4 -s 32 -r 2 -n 100 -x 600 -v 8 -c 0.9 -p 3". SOAP coverage software was then used to calculate the read coverage of each genome, normalized by genome length, and further normalized to the relative abundance for each individual sample. The profile was generated based on uniquely-mapped reads only.

3.3 Identification of Colorectal Cancer-Associated MLG Species

Based on the identified 140,455 colorectal cancer associated maker genes profile, the inventors constructed the colorectal cancer-associated MLGs using the method described in the previous type 2 diabetes study (Qin et al. 2012, supra). All of the genes were aligned to the reference genomes of the IMG database v400 to obtain genome-level annotation. An MLG was assigned to a genome if>50% constitutive genes were annotated to that genome, otherwise the genome was labeled unclassified. A total of 87 MLGs with a gene number over 100 were selected as colorectal cancer-associated MLGs. These MLGs were grouped based on the species annotations of these genomes to construct MLG species.

To estimate the relative abundance of an MLG species, the inventors estimated the average abundance of the genes of the MLG species, after removing the genes with the 5% lowest and 5% highest abundance. The relative abundance of the IMG species was estimated by summing the abundance of the IMG genomes belonging to that species.

Figure 7:
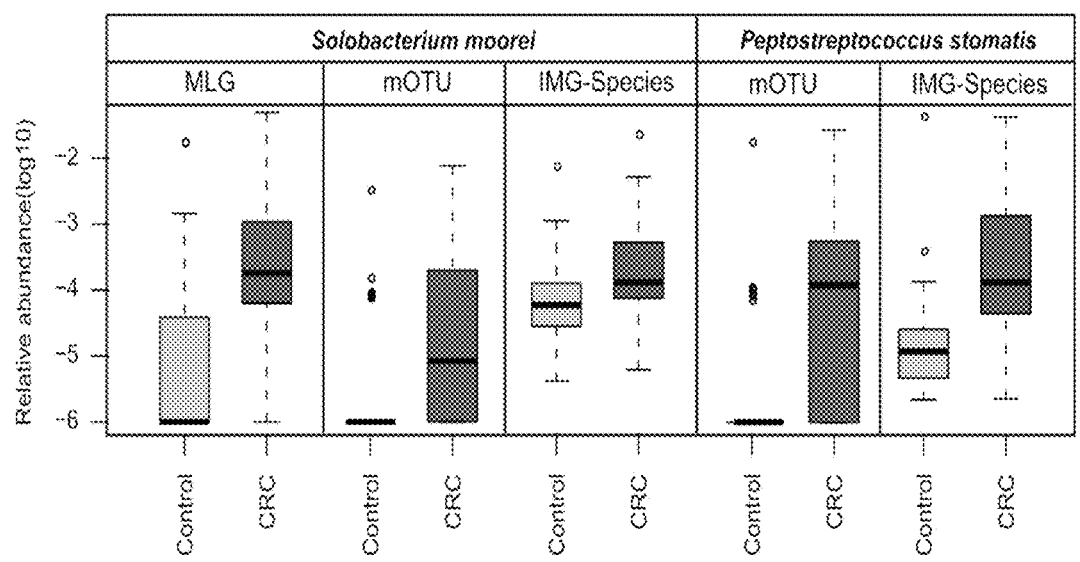
FIG. 7 shows the enrichment of *Solobacterium moore* and *Peptostreptococcus stomati* in the CRC patient microbiomes.

These analyses identified 30 IMG species, 21 mOTUs and 86 MLG species that were significantly associated with CRC status (Wilcoxon rank-sum test, $q<0.05$; see Tables 10, 11). *Eubacterium ventriosum* was consistently enriched in the control microbiomes using all three methods (Wilcoxon rank-sum tests—IMG: $q=0.0414$; mOTU: $q=0.012757$; MLG: $q=5.446\times10^{-4}$), and *Eubacterium eligens* was enriched according to two methods (Wilcoxon rank-sum tests—IMG: $q=0.069$; MLG: $q=0.00031$). Conversely, *Parvimonas micra* ($q<1.80\times10^{-5}$), *Peptostreptococcus stomatis* ($q<1.80\times10^{-5}$), *Solobacterium moorei* ($q<0.004331$) and *Fusobacterium nucleatum* ($q<0.004565$) were consistently enriched in CRC patient microbiomes using all three methods (FIG. 6, FIG. 7). *P. stomatis* has been associated with oral cancer, and *S. moorei* has been associated with bacteremia. Recent work using 16S rRNA sequencing has reported a significant enrichment of *F. nucleatum* in CRC tumor samples, and this bacteria has been shown to possess adhesive, invasive and pro-inflammatory properties. The inventors' results confirmed this association in a new cohort with different genetic and cultural origins. However, the highly-significant enrichment of *P. micra*—an obligate anaerobic bacterium that can cause oral infections like *F. nucleatum*—in CRC-associated microbiomes is a novel finding. *P. micra* is involved in the etiology of periodontis, and it produces a wide range of proteolytic enzymes and uses peptones and amino acids as an energy source. It is known to produce hydrogen sulphide, which promotes tumor growth and the proliferation of colon cancer cells. Further research is required to verify whether *P. micra* is involved in the pathogenesis of CRC, or if its enrichment is a result of CRC-associated changes in the colon and/or rectum. Nevertheless, it represents a potential biomarker for non-invasive diagnosis of CRC.

3.4 Species Marker Identification

In order to evaluate the predictive power of these taxonomic associations, the inventors used the random forest ensemble learning method (D. Knights, E. K. Costello, R. Knight (2011), "Supervised classification of human microbiota," *FEMS microbiology reviews*, 35, 343, incorporated herein by reference) to identify key species markers in the species profiles from the three different methods.

3.4.1 MLG Species Marker Identification

Based on the constructed 87 MLGs with gene numbers over 100, the inventors performed the Wilcoxon rank-sum test on each MLG using a Benjamini-Hochberg adjustment, and 86 MLGs were selected as colorectal-associated MLGs with $q<0.05$. To identify MLG species markers, the inventors used the "randomForest 4.5-36" function of R vision 2.10 to analyze the 86 colorectal cancer-associated MLG species. Firstly, the inventors sorted all of the 86 MLG species by the importance given by the "randomForest" method. MLG marker sets were constructed by creating incremental subsets of the top ranked MLG species, starting from 1 MLG species and ending at 86 MLG species.

For each MLG marker set, the inventors calculated the false predication ratio in the 128 Chinese cohorts (cohort 1). Finally, the MLG species sets with the lowest false prediction ratio were selected as MLG species markers. Furthermore, the inventors drew the ROC curve using the probability of illness based on the selected MLG species markers.

3.4.2 IMG Species and mOTU Species Markers Identification

Based on the IMG species and mOTU species profiles, the inventors identified the colorectal cancer-associated IMG species and mOTU species with $q<0.05$ (Wilcoxon rank-sum test with 6 Benjamini-Hochberg adjustment). Subsequently, the IMG species markers and the mOTU species markers were selecting using the random forest approach as in the MLG species markers selection.

This analysis revealed that 16 IMG species, 10 species-level mOTUs and 21 MLG species were highly predictive of CRC status (Tables 12, 13), with a predictive power of 0.86, 0.90 and 0.94 in ROC analysis, respectively (FIG. 8). *Parvimonas micra* was identified as a key species from all three methods, and *Fusobacterium nucleatum* and *Solobacterium moorei* from two out of three methods, providing further statistical support for their association with CRC status.

3.5 MLG, IMG and mOTU Species Stage Enrichment Analysis

Encouraged by the consistent species associations with CRC status and to take advantage of the records of disease stages of the CRC patients (Table 2), the inventors explored the species profiles for specific signatures identifying early stages of CRC. The inventors hypothesized that such an effort might even reveal stage-specific associations that are difficult to identify in a global analysis. To identify which species were enriched in the four colorectal cancer stages or in healthy controls, the inventors carried out a Kruskal test for the MLG species with a gene number over 100, and all of the IMG species and mOTU species with q<0.05 (Wilcoxon rank-sum test with Benjamini-Hochberg adjustment) to obtain the species enrichment information using the highest rank mean among the four CRC stages and the control. The inventors also compared the significance between every two groups by a pair-wise Wilcoxon Rank sum test.

In Chinese cohort I, several species showed significantly different abundances in the different CRC stages. Among these, the inventors did not identify any species enriched in stage I compared to the other CRC stages and the control samples. *Peptostreptococcus stomatis*, *Prevotella nigrescens* and *Clostridium symbiosum* were enriched in stage II or later compared to the control samples, suggesting that they colonize the colon/rectum after the onset of CRC (FIG. 9). However, *Fusobacterium nucleatum*, *Parvimonas micra*, and *Solobacterium moorei* were enriched in all four stages compared to the control samples and were most abundant in stage II (FIG. 10), suggesting that they play a role in both CRC etiology and pathogenesis, and implicating them as potential biomarkers for early CRC.

EXAMPLE 4

Validation of Markers by qPCR

The 31 gene biomarkers were derived using the admittedly expensive deep metagenome sequencing approach. Translating them into diagnostic biomarkers would require reliable detection using more simple and less expensive methods such as quantitative PCR (TaqMan probe-based qPCR). Primers and probes were designed using Primer Express v3.0 (Applied Biosystems, Foster City, Calif., USA). The qPCR was performed on an ABI7500 Real-Time PCR System using the TaqMan® Universal PCR Master Mixreagent (Applied Biosystems). Universal 16S rDNA was used as an internal control, and the abundance of gene markers were expressed as relative levels to 16S rDNA.

To validate the test, the inventors selected two case-enriched gene markers (m482585(SEQ ID NO: 10) and m1704941(SEQ ID NO: 14)) and measured their abundance by qPCR in a subset of 100 samples (55 cases and 45 controls). Quantification of each of the two genes using the two platforms (metagenomic sequencing and qPCR) showed strong correlations (Spearman r=0.93-0.95, FIG. 11), suggesting that the gene markers could also be reliably measured using qPCR.

Next, in order to validate the markers in previously unseen samples, the inventors measured the abundance of these two gene markers using qPCR in 164 fecal samples (51 cases and 113 controls) from an independent Chinese cohort (cohort II). Two case-enriched gene markers significantly associated with CRC status, at significance levels of q=6.56×10$^{-9}$ (m1704941, butyryl-CoA dehydrogenase from *F. nucleatum*), and q=0.0011 (m482585, RNA-directed DNA polymerase from an unknown microbe). The gene from *F. nucleatum* was present in only 4 out of 113 control microbiomes, suggesting a potential for developing specific diagnostic tests for CRC using fecal samples. The CRC index based on the combined qPCR abundance of the two case-enriched gene markers separated the CRC samples from control samples in cohort II (Wilcoxon rank-sum test, P=4.01×10$^{-7}$; FIG. 12A). However, the moderate classification potential (inferred from area under the ROC curve of 0.73; FIG. 12B) using only these two genes suggested that additional biomarkers could improve the classification of CRC patient microbiomes.

Another gene from *P. micra* was the highly conserved rpoB gene (namely m1696299 (SEQ ID NO: 6), with identity of 99.78%) encoding RNA polymerase subunit β, often used as a phylogenetic marker (F. D. Ciccarelli et al. (2006), "Toward automatic reconstruction of a highly resolved tree of life," *Science*, 311, 1283, incorporated herein by reference). Since the inventors repeatedly identified *P. micra* as a novel biomarker for CRC using several strategies including species-agnostic procedures, the inventors performed an additional qPCR experiment for this marker gene on Chinese cohort II as described above and found a significant enrichment in CRC patient microbiomes (Wilcoxon rank-sum test, P=2.15×10$^{-15}$). When the inventors combined this gene with the two qPCR-validated genes, the CRC index from these three genes clearly separated case from control samples in Chinese cohort II (Wilcoxon rank-sum test, P=5.76×10$^{-13}$, FIG. 13A, Table 14) and showed reliable classification potential with an improved area under the ROC curve of 0.84 (best cutoff: −14.39, FIG. 13B). The CRC index of each sample was calculated by the formula below:

$$I_j = \frac{\sum_i \epsilon_N \log 10(A_{ij} + 10^{-20})}{|N|},$$

wherein:
$A_{ij}$ is the qPCR abundance of marker gene i in sample j, wherein i refers to each of the marker genes as set forth in the gene marker set,
N is a subset of all of the patient-enriched markers, such as the CRC-associated marker genes, the subset of CRC-associated markers can comprise the marker genes having the nucleotide sequences of SEQ ID NOs: 10, SEQ ID NO: 14 and SEQ ID NO:6, respectively,
|N| is the number (size) of the biomarkers in the subset, wherein |N| is 3 ,
wherein an index greater than a cutoff indicates that the subject has or is at the risk of developing colorectal cancer.

The abundance of rpoB from *P. micro* was significantly higher compared to control samples starting from stage II CRC samples (FIG. 13C, Table 14), consistent with the inventors' results from species abundance analysis, and providing further evidence that this gene could serve as a non-invasive biomarker for the identification of early stage CRC.

TABLE 15

Sequence Information for the primers and probes for the selected 3 gene markers

| >1696299 | Forward | AAGAATGGAGAGAGTTGTTAGAGAAAGAA (SEQ ID NO: 32) |
|---|---|---|
| | Reverse | TTGTGATAATTGTGAAGAACCGAAGA (SEQ ID NO: 33) |
| | Probe | AACTCAAGATCCAGACCTTGCTACGCCTCA (SEQ ID NO: 34) |

TABLE 15-continued

Sequence Information for the primers and probes for the selected 3 gene markers

| >1704941 | Forward | TTGTAAGTGCTGGTAAAGGGATTG (SEQ ID NO: 35) |
| --- | --- | --- |
| | Reverse | CATTCCTACATAACGGTCAAGAGGTA (SEQ ID NO: 36) |
| | Probe | AGCTTCTATTGGTTCTTCTCGTCCAGTGGC (SEQ ID NO: 37) |
| >482585 | Forward | AATGGGAATGGAGCGGATTC (SEQ ID NO: 38) |
| | Reverse | CCTGCACCAGCTTATCGTCAA (SEQ ID NO: 39) |
| | Probe | AAGCCTGCGGAACCACAGTTACCAGC (SEQ ID NO: 40) |

TABLE 5

The 31 gene markers identified by the mRMR feature selection method. Detailed information regarding their enrichment, occurrence in colorectal cancer cases and controls, a statistical test of association, taxonomy and identity percentage are listed.

| Marker gene ID | Wilcoxon Test P | | Enrich | Occurrence | | | |
| --- | --- | --- | --- | --- | --- | --- | --- |
| | P-value | q-value | | Control (n = 54) | | Case (n = 74) | |
| | | | | Count | Rate (%) | Count | Rate (%) |
| 3546943 | 1.59E−06 | 1.90465E−06 | Case | 3 | 5.56 | 27 | 36.49 |
| 1225574 | 1.47E−06 | 1.8957E−06 | Case | 0 | 0.00 | 13 | 17.57 |
| 2736705 | 5.35E−07 | 8.4594E−07 | Case | 0 | 0.00 | 21 | 28.38 |
| 2748108 | 2.12E−07 | 4.38881E−07 | Case | 0 | 0.00 | 20 | 27.03 |
| 2040133 | 7.46E−11 | 7.70506E−10 | Case | 7 | 12.96 | 44 | 59.46 |
| 1694820 | 9.78E−08 | 2.52552E−07 | Case | 1 | 1.85 | 18 | 24.32 |
| 1704941 | 1.16E−08 | 5.12764E−08 | Case | 1 | 1.85 | 21 | 28.38 |
| 482585 | 3.81E−09 | 2.36224E−08 | Case | 9 | 16.67 | 50 | 67.57 |
| 3246804 | 4.19E−08 | 1.44418E−07 | Case | 1 | 1.85 | 24 | 32.43 |
| 1696299 | 8.50E−10 | 6.58857E−09 | Case | 1 | 1.85 | 33 | 44.59 |
| 1699104 | 1.00E−08 | 5.12764E−08 | Case | 1 | 1.85 | 31 | 41.89 |
| 2361423 | 4.89E−13 | 1.51641E−11 | Case | 7 | 12.96 | 55 | 74.32 |
| 3173495 | 1.14E−12 | 1.77065E−11 | Case | 4 | 7.41 | 44 | 59.46 |
| 3494506 | 4.93E−06 | 5.27005E−06 | Control | 19 | 35.19 | 4 | 5.41 |
| 2211919 | 3.59E−08 | 1.3927E−07 | Control | 49 | 90.74 | 39 | 52.70 |
| 2206475 | 6.49E−07 | 9.58475E−07 | Control | 23 | 42.59 | 5 | 6.76 |
| 3976414 | 1.57E−07 | 3.48653E−07 | Control | 15 | 27.78 | 3 | 4.05 |
| 3319172 | 1.12E−07 | 2.666E−07 | Control | 19 | 35.19 | 2 | 2.70 |
| 3319526 | 7.04E−08 | 1.98403E−07 | Control | 21 | 38.89 | 7 | 9.46 |
| 4171064 | 4.69E−08 | 1.45363E−07 | Control | 29 | 53.70 | 10 | 13.51 |
| 370640 | 4.06E−06 | 4.49308E−06 | Control | 12 | 22.22 | 0 | 0.00 |
| 1804565 | 7.31E−07 | 9.85539E−07 | Control | 16 | 29.63 | 1 | 1.35 |
| 3399273 | 4.88E−07 | 8.40846E−07 | Control | 41 | 75.93 | 23 | 31.08 |
| 3531210 | 9.76E−06 | 9.75675E−06 | Control | 8 | 14.81 | 0 | 0.00 |
| 3611706 | 1.67E−06 | 1.91677E−06 | Control | 13 | 24.07 | 0 | 0.00 |
| 3840474 | 9.76E−06 | 9.75675E−06 | Control | 6 | 11.11 | 0 | 0.00 |
| 4148945 | 5.46E−07 | 8.4594E−07 | Control | 23 | 42.59 | 8 | 10.81 |
| 4165909 | 1.60E−06 | 1.90465E−06 | Control | 8 | 14.81 | 0 | 0.00 |
| 4256106 | 3.69E−07 | 6.72327E−07 | Control | 21 | 38.89 | 4 | 5.41 |
| 181682 | 6.97E−07 | 9.82079E−07 | Control | 27 | 50.00 | 8 | 10.81 |
| 1559769 | 2.83E−07 | 5.48673E−07 | Control | 17 | 31.48 | 5 | 6.76 |

| Marker gene ID | Blastn to IMG v400 | | Blastp to KEGG v59 |
| --- | --- | --- | --- |
| | Identity | Taxonomy | Description |
| 3546943 | 99.09 | *Bacteroides* sp. 2_1_56FAA | zinc protease |
| 1225574 | 88.88 | *Clostridium hathewayi* DSM 13479 | lactose/L-arabinose transport system substrate-binding protein |
| 2736705 | 99.68 | *Clostridium hathewayi* DSM 13479 | NA |
| 2748108 | 99.82 | *Clostridium hathewayi* DSM 13479 | RNA polymerase sigma-70 factor, ECF subfamily |
| 2040133 | 99.4 | *Clostridium symbiosum* WAL-14163 | cobalt/nickel transport system permease protein |
| 1694820 | 99.17 | *Fusobacterium* sp. 7_1 | V-type H+-transporting ATPase subunit K |
| 1704941 | 99.13 | *Fusobacterium nucleatum vincentii* ATCC 49256 | butyryl-CoA dehydrogenase |
| 482585 | NA | NA | RNA-directed DNA polymerase |
| 3246804 | NA | NA | citrate-Mg2+:H+ or citrate-Ca2+:H+ symporter, CitMHS family |
| 1696299 | 99.78 | *Parvimonas micra* ATCC 33270 | DNA-directed RNA polymerase subunit beta |

TABLE 5-continued

The 31 gene markers identified by the mRMR feature selection method. Detailed information regarding their enrichment, occurrence in colorectal cancer cases and controls, a statistical test of association, taxonomy and identity percentage are listed.

| | | | |
|---|---|---|---|
| 1699104 | 98.08 | *Parvimonas micra* ATCC 33270 | glutamate decarboxylase |
| 2361423 | 93.87 | *Peptostreptococcus anaerobius* 653-L | transposase |
| 3173495 | 93.98 | *Peptostreptococcus anaerobius* 653-L | transposase |
| 3494506 | 90.37 | Burkholderiales bacterium 1_1_47 | ribosomal small subunit pseudouridine synthase A |
| 2211919 | 80.99 | *Coprobacillus* sp. 8_2_54BFAA | NA |
| 2206475 | 98.59 | *Eubacterium ventriosum* ATCC 27560 | beta-glucosidase |
| 3976414 | 87.12 | *Faecalibacterium* cf. *prausnitzii* KLE1255 | adenosylcobinamide-phosphate synthase CobD |
| 3319172 | 84.22 | *Faecalibacterium prausnitzii* A2-165 | UDP-N-acetylmuramoylalanyl-D-glutamyl-2,6-diaminopimelate--D-alanyl-D-alanine ligase |
| 3319526 | 90.01 | *Faecalibacterium prausnitzii* L2-6 | replicative DNA helicase |
| 4171064 | 94.94 | *Faecalibacterium prausnitzii* L2-6 | cytidine deaminase |
| 370640 | 99.4 | *Bacteroides clarus* YIT 12056 | NA |
| 1804565 | NA | NA | branched-chain amino acid transport system ATP-binding protein |
| 3399273 | NA | NA | two-component system, LytT family, response regulator |
| 3531210 | NA | NA | GDP-L-fucose synthase |
| 3611706 | NA | NA | anti-repressor protein |
| 3840474 | NA | NA | NA |
| 4148945 | NA | NA | NA |
| 4165909 | NA | NA | N-acetylmuramoyl-L-alanine amidase |
| 4256106 | NA | NA | integrase/recombinase XerD |
| 181682 | 99.25 | *Roseburia intestinalis* L1-82 | NA |
| 1559769 | 88.65 | *Coprococcus catus* GD/7 | polar amino acid transport system substrate-binding protein |

TABLE 7

CRC index estimated in CRC, T2D and IBD patients and healthy cohorts.

| | | Comparison with CRC patients | |
|---|---|---|---|
| Cohort/group | Median CRC index | P-value | q-value |
| CRC patients | 6.420958803 | NA | NA |
| CRC controls | −5.476945331 | 1.96E−21 | 2.44E−21 |
| T2D patients | −0.108110996 | 1.33E−27 | 2.21E−27 |
| T2D controls | −1.471692382 | 6.21E−31 | 3.11E−30 |
| IBD patients | −2.214296342 | 2.38E−10 | 2.38E−10 |
| IBD controls | −4.724156396 | 7.56E−29 | 1.89E−28 |

TABLE 10

IMG and mOTU species associated with CRC with q-value <0.05

| | Control rank mean | Case rank mean | Enrichment (1: Control; 0: Case) | P-value | q-value |
|---|---|---|---|---|---|
| 30 IMG species | | | | | |
| *Peptostreptococcus stomatis* | 37.25926 | 84.37838 | 0 | 1.29E−12 | 3.34E−09 |
| *Parvimonas micra* | 38.43519 | 83.52027 | 0 | 1.13E−11 | 1.46E−08 |
| *Parvimonas* sp. oral taxon 393 | 39.81481 | 82.51351 | 0 | 1.28E−10 | 1.10E−07 |
| *Parvimonas* sp. oral taxon 110 | 43.52778 | 79.80405 | 0 | 4.71E−08 | 3.04E−05 |
| *Gemella morbillorum* | 43.87037 | 79.55405 | 0 | 7.77E−08 | 4.01E−05 |
| *Burkholderia mallei* | 45.19444 | 78.58784 | 0 | 4.84E−07 | 0.000156 |
| *Fusobacterium* sp. oral taxon 370 | 45.02778 | 78.70946 | 0 | 3.93E−07 | 0.000156 |
| *Fusobacterium nucleatum* | 45.09259 | 78.66216 | 0 | 4.33E−07 | 0.000156 |
| *Leptotrichia buccalis* | 45.60185 | 78.29054 | 0 | 7.30E−07 | 0.000209 |
| *Beggiatoa* sp. PS | 46.53704 | 77.60811 | 0 | 2.79E−06 | 0.000601 |
| *Prevotella intermedia* | 46.47222 | 77.65541 | 0 | 2.67E−06 | 0.000601 |

TABLE 10-continued

IMG and mOTU species associated with CRC with q-value <0.05

|  | Control rank mean | Case rank mean | Enrichment (1: Control; 0: Case) | P-value | q-value |
|---|---|---|---|---|---|
| *Streptococcus dysgalactiae* | 47.06481 | 77.22297 | 0 | 3.09E-06 | 0.000613 |
| *Streptococcus pseudoporcinus* | 47.5 | 76.90541 | 0 | 8.58E-06 | 0.001581 |
| *Paracoccus denitrificans* | 47.48148 | 76.91892 | 0 | 9.35E-06 | 0.001608 |
| *Solobacterium moorei* | 47.66667 | 76.78378 | 0 | 1.17E-05 | 0.001884 |
| *Streptococcus constellatus* | 48.2037 | 76.39189 | 0 | 2.20E-05 | 0.003153 |
| *Crenothrix polyspora* | 48.76852 | 75.97973 | 0 | 4.20E-05 | 0.005697 |
| *Filifactor alocis* | 49.06481 | 75.76351 | 0 | 5.84E-05 | 0.007533 |
| *Sulfurovum* sp. SCGC AAA036-O23 | 52.12037 | 73.53378 | 0 | 6.60E-05 | 0.008105 |
| *Clostridium hathewayi* | 49.68519 | 75.31081 | 0 | 0.000115 | 0.013431 |
| Lachnospiraceae bacterium 5_1_57FAA | 50.10185 | 75.00676 | 0 | 0.000178 | 0.019084 |
| *Peptostreptococcus anaerobius* | 50.14815 | 74.97297 | 0 | 0.000186 | 0.019221 |
| *Streptococcus equi* | 50.58333 | 74.65541 | 0 | 0.00029 | 0.027747 |
| *Streptococcus anginosus* | 50.66667 | 74.59459 | 0 | 0.000316 | 0.029114 |
| *Leptotrichia hofstadii* | 50.99074 | 74.35811 | 0 | 0.000342 | 0.030424 |
| *Peptoniphilus indolicus* | 51.2963 | 74.13514 | 0 | 0.000581 | 0.048307 |
| *Eubacterium ventriosum* | 80.98148 | 52.47297 | 1 | 1.77E-05 | 0.00269 |
| *Adhaeribacter aquaticus* | 77.06481 | 55.33108 | 1 | 0.000271 | 0.026839 |
| *Eubacterium eligens* | 77.90741 | 54.71622 | 1 | 0.000482 | 0.041404 |
| *Haemophilus sputorum* | 77.66667 | 54.89189 | 1 | 0.000608 | 0.048977 |
| 21 mOTU species | | | | | |
| *Parvimonas micra* | 46.2963 | 77.78378 | 0 | 4.11E-08 | 1.80E-05 |
| *Peptostreptococcus stomatis* | 46.25 | 77.81757 | 0 | 6.56E-08 | 1.80E-05 |
| motu_linkage_group_731 | 50.42593 | 74.77027 | 0 | 1.08E-06 | 0.000198 |
| *Gemella morbillorum* | 47.93519 | 76.58784 | 0 | 1.57E-06 | 0.000215 |
| *Clostridium symbiosum* | 48.66667 | 76.05405 | 0 | 1.89E-05 | 0.00173 |
| *Solobacterium moorei* | 51.22222 | 74.18919 | 0 | 6.31E-05 | 0.004331 |
| *Fusobacterium nucleatum* | 54.62037 | 71.70946 | 0 | 9.15E-05 | 0.004565 |
| unclassified *Fusobacterium* | 54.22222 | 72 | 0 | 0.000176 | 0.00806 |
| *Clostridium ramosum* | 50.92593 | 74.40541 | 0 | 0.000289 | 0.012202 |
| Clostridiales bacterium 1_7_47FAA | 51.27778 | 74.14865 | 0 | 0.000365 | 0.013366 |
| *Bacteroides fragilis* | 51.09259 | 74.28378 | 0 | 0.00045 | 0.01371 |
| motu_linkage_group_624 | 51.01852 | 74.33784 | 0 | 0.000448 | 0.01371 |
| *Clostridium bolteae* | 51.81481 | 73.75676 | 0 | 0.000952 | 0.026134 |
| motu_linkage_group_407 | 81.13889 | 52.35811 | 1 | 6.00E-06 | 0.000659 |
| motu_linkage_group_490 | 80.46296 | 52.85135 | 1 | 3.06E-05 | 0.002403 |
| motu_linkage_group_316 | 79.61111 | 53.47297 | 1 | 8.17E-05 | 0.004487 |
| motu_linkage_group_443 | 79.66667 | 53.43243 | 1 | 7.63E-05 | 0.004487 |
| *Eubacterium ventriosum* | 78.09259 | 54.58108 | 1 | 0.000325 | 0.012757 |
| motu_linkage_group_510 | 77.84259 | 54.76351 | 1 | 0.000443 | 0.01371 |
| motu_linkage_group_611 | 77.2963 | 55.16216 | 1 | 0.000606 | 0.017499 |
| motu_linkage_group_190 | 75.16667 | 56.71622 | 1 | 0.001694 | 0.044273 |

TABLE 11

List of 86 MLG species formed after grouping MLGs with more than 100 genes using the species annotation when available.

|  | Control rank mean | Case rank mean | Enrichment (1: Control; 0: Case) | P-value | q-value |
|---|---|---|---|---|---|
| *Parvimonas micra* | 38.40741 | 83.54054 | 0 | 3.16E-12 | 2.75E-10 |
| *Fusobacterium nucleatum* | 40.32407 | 82.14189 | 0 | 2.97E-11 | 1.29E-09 |
| *Solobacterium moorei* | 42.2037 | 80.77027 | 0 | 3.85E-09 | 1.12E-07 |
| *Clostridium symbiosum* | 46.31481 | 77.77027 | 0 | 1.64E-06 | 3.56E-05 |
| CRC 2881 | 51.25926 | 74.16216 | 0 | 2.57E-06 | 4.46E-05 |
| *Clostridium hathewayi* | 46.77778 | 77.43243 | 0 | 3.92E-06 | 5.69E-05 |
| CRC 6481 | 52.09259 | 73.55405 | 0 | 1.36E-05 | 0.000107 |
| *Clostridium clostridioforme* | 50.2037 | 74.93243 | 0 | 1.27E-05 | 0.000107 |
| Clostridiales bacterium 1_7_47FAA | 48.16667 | 76.41892 | 0 | 2.02E-05 | 0.000135 |
| *Clostridium* sp. HGF2 | 48.27778 | 76.33784 | 0 | 2.36E-05 | 0.000147 |
| CRC 2794 | 51.03704 | 74.32432 | 0 | 3.50E-05 | 0.000179 |
| CRC 4136 | 50.99074 | 74.35811 | 0 | 5.22E-05 | 0.000233 |
| *Bacteroides fragilis* | 49.09259 | 75.74324 | 0 | 5.97E-05 | 0.000236 |
| Lachnospiraceae bacterium 5_1_57FAA | 49.96296 | 75.10811 | 0 | 7.37E-05 | 0.000273 |
| *Desulfovibrio* sp. 6_1_46AFAA | 53.33333 | 72.64865 | 0 | 0.000214 | 0.000546 |
| *Coprobacillus* sp. 3_3_56FAA | 50.53704 | 74.68919 | 0 | 0.000265 | 0.000623 |
| *Cloacibacillus evryensis* | 52.73148 | 73.08784 | 0 | 0.000359 | 0.000801 |
| CRC 2867 | 52.31481 | 73.39189 | 0 | 0.000552 | 0.001162 |
| *Fusobacterium varium* | 54.57407 | 71.74324 | 0 | 0.000586 | 0.001186 |
| *Clostridium bolteae* | 51.39815 | 74.06081 | 0 | 0.000647 | 0.001223 |
| *Subdoligranulum* sp. 4_3_54A2FAA | 51.56481 | 73.93919 | 0 | 0.000758 | 0.001373 |
| *Clostridium citroniae* | 51.71296 | 73.83108 | 0 | 0.000861 | 0.001529 |

TABLE 11-continued

List of 86 MLG species formed after grouping MLGs with more than 100 genes using the species annotation when available.

|  | Control rank mean | Case rank mean | Enrichment (1: Control; 0: Case) | P-value | q-value |
| --- | --- | --- | --- | --- | --- |
| Lachnospiraceae bacterium 8_1_57FAA | 51.88889 | 73.7027 | 0 | 0.001024 | 0.001782 |
| Streptococcus equinus | 54.52778 | 71.77703 | 0 | 0.001581 | 0.002457 |
| CRC 4069 | 53.7963 | 72.31081 | 0 | 0.001632 | 0.00249 |
| Lachnospiraceae bacterium 3_1_46FAA | 52.53704 | 73.22973 | 0 | 0.00178 | 0.002612 |
| Dorea formicigenerans | 52.98148 | 72.90541 | 0 | 0.002703 | 0.003409 |
| Synergistes sp. 3_1 syn1 | 54.37963 | 71.88514 | 0 | 0.003358 | 0.004002 |
| Lachnospiraceae bacterium 3_1_57FAA_CT1 | 54.07407 | 72.10811 | 0 | 0.004478 | 0.005109 |
| CRC 3579 | 54.05556 | 72.12162 | 0 | 0.005638 | 0.006289 |
| Alistipes indistinctus | 54.50926 | 71.79054 | 0 | 0.008262 | 0.008766 |
| Con 10180 | 82.03704 | 51.7027 | 1 | 4.87E−06 | 6.05E−05 |
| Coprococcus sp. ART55/1 | 80.85185 | 52.56757 | 1 | 8.22E−06 | 8.94E−05 |
| Con 7958 | 75.27778 | 56.63514 | 1 | 1.36E−05 | 0.000107 |
| butyrate-producing bacterium SS3/4 | 80.57407 | 52.77027 | 1 | 1.98E−05 | 0.000135 |
| Haemophilus parainfluenzae | 80.49074 | 52.83108 | 1 | 2.54E−05 | 0.000148 |
| Con 154 | 80.35185 | 52.93243 | 1 | 3.30E−05 | 0.000179 |
| Con 4595 | 77.21296 | 55.22297 | 1 | 4.17E−05 | 0.000202 |
| Con 1617 | 76.12963 | 56.01351 | 1 | 5.61E−05 | 0.000233 |
| Con 1979 | 79.94444 | 53.22973 | 1 | 5.62E−05 | 0.000233 |
| Con 1371 | 78.46296 | 54.31081 | 1 | 7.54E−05 | 0.000273 |
| Con 1529 | 75.05556 | 56.7973 | 1 | 9.25E−05 | 0.00031 |
| Eubacterium eligens | 79.53704 | 53.52703 | 1 | 9.03E−05 | 0.00031 |
| Con 1987 | 79.42593 | 53.60811 | 1 | 0.000101 | 0.000324 |
| Con 5770 | 79.39815 | 53.62838 | 1 | 0.000104 | 0.000324 |
| Con 1197 | 75.42593 | 56.52703 | 1 | 0.000128 | 0.000383 |
| Con 4699 | 78.78704 | 54.07432 | 1 | 0.000152 | 0.000441 |
| Clostridium sp. L2-50 | 76.37963 | 55.83108 | 1 | 0.000167 | 0.000469 |
| Con 2606 | 77.5 | 55.01351 | 1 | 0.000189 | 0.000514 |
| Eubacterium ventriosum | 78.62963 | 54.18919 | 1 | 0.000207 | 0.000545 |
| Bacteroides clarus | 75.55556 | 56.43243 | 1 | 0.000247 | 0.000597 |
| Eubacterium biforme | 74.68519 | 57.06757 | 1 | 0.000247 | 0.000597 |
| Faecalibacterium prausnitzii | 78.25926 | 54.45946 | 1 | 0.00034 | 0.000779 |
| Con 563 | 72.7037 | 58.51351 | 1 | 0.000556 | 0.001162 |
| Con 6037 | 77.5463 | 54.97973 | 1 | 0.000561 | 0.001162 |
| Con 8757 | 77.17593 | 55.25 | 1 | 0.000634 | 0.001223 |
| Ruminococcus obeum | 77.53704 | 54.98649 | 1 | 0.000629 | 0.001223 |
| Con 1513 | 76.59259 | 55.67568 | 1 | 0.000701 | 0.001298 |
| Roseburia intestinalis | 76.99074 | 55.38514 | 1 | 0.001079 | 0.001841 |
| Ruminococcus torques | 76.92593 | 55.43243 | 1 | 0.001186 | 0.001984 |
| Con 4829 | 76.7963 | 55.52703 | 1 | 0.001335 | 0.002151 |
| Con 569 | 73.41667 | 57.99324 | 1 | 0.001334 | 0.002151 |
| Con 10559 | 76.59259 | 55.67568 | 1 | 0.001561 | 0.002457 |
| Con 1604 | 71.92593 | 59.08108 | 1 | 0.001781 | 0.002612 |
| Con 2494 | 74.35185 | 57.31081 | 1 | 0.001802 | 0.002612 |
| Con 1867 | 76.38889 | 55.82432 | 1 | 0.001908 | 0.002722 |
| Con 1241 | 76.27778 | 55.90541 | 1 | 0.002132 | 0.00294 |
| Con 5752 | 73.65741 | 57.81757 | 1 | 0.002163 | 0.00294 |
| Con 7367 | 76.23148 | 55.93919 | 1 | 0.002112 | 0.00294 |
| Con 6128 | 76.22222 | 55.94595 | 1 | 0.002274 | 0.003043 |
| Con 5615 | 76.07407 | 56.05405 | 1 | 0.002372 | 0.003104 |
| Klebsiella pneumoniae | 74.7037 | 57.05405 | 1 | 0.00239 | 0.003104 |
| Con 4909 | 75.72222 | 56.31081 | 1 | 0.002685 | 0.003409 |
| Con 356 | 75.94444 | 56.14865 | 1 | 0.002808 | 0.00349 |
| Eubacterium rectale | 75.90741 | 56.17568 | 1 | 0.002953 | 0.003619 |
| Con 6068 | 75.74074 | 56.2973 | 1 | 0.003338 | 0.004002 |
| Con 4295 | 74.98148 | 56.85135 | 1 | 0.004171 | 0.004904 |
| Con 2703 | 74.55556 | 57.16216 | 1 | 0.00437 | 0.005069 |
| Con 2503 | 74.14815 | 57.45946 | 1 | 0.004522 | 0.005109 |
| Con 631 | 70.01852 | 60.47297 | 1 | 0.006178 | 0.006804 |
| Con 561 | 70.5 | 60.12162 | 1 | 0.008137 | 0.00874 |
| Con 8420 | 72.64815 | 58.55405 | 1 | 0.008068 | 0.00874 |
| Con 425 | 73.19444 | 58.15541 | 1 | 0.008397 | 0.008802 |
| Con 7993 | 73.74074 | 57.75676 | 1 | 0.009358 | 0.009692 |
| Burkholderiales bacterium 1_1_47 | 72.37963 | 58.75 | 1 | 0.009707 | 0.009935 |
| Con 600 | 69.53704 | 60.82432 | 1 | 0.026354 | 0.02666 |

TABLE 12

IMG and mOTU species makers. IMG and mOTU species markers identified using the random forest method among species associated with CRC (Table S9). Species markers were listed by their importance reported by the method.

| | Control rank mean | Case rank mean | Enrichment (1: Control; 0: Case) | P-value | q-value |
|---|---|---|---|---|---|
| 16 IMG species makers | | | | | |
| *Peptostreptococcus stomatic* | 37.25926 | 84.37838 | 0 | 1.29E−12 | 3.34E−09 |
| *Parvimonas micra* | 38.43519 | 83.52027 | 0 | 1.13E−11 | 1.46E−08 |
| *Parvimonas* sp. oral taxon 393 | 39.81481 | 82.51351 | 0 | 1.28E−10 | 1.10E−07 |
| *Parvimonas* sp. oral taxon 110 | 43.52778 | 79.80405 | 0 | 4.71E−08 | 3.04E−05 |
| *Gemella morbillorum* | 43.87037 | 79.55405 | 0 | 7.77E−08 | 4.01E−05 |
| *Fusobacterium* sp. oral taxon 370 | 45.02778 | 78.70946 | 0 | 3.93E−07 | 1.56E−04 |
| *Burkholderia mallei* | 45.19444 | 78.58784 | 0 | 4.84E−07 | 1.56E−04 |
| *Fusobacterium nucleatum* | 45.09259 | 78.66216 | 0 | 4.33E−07 | 1.56E−04 |
| *Leptotrichia buccalis* | 45.60185 | 78.29054 | 0 | 7.30E−07 | 2.09E−04 |
| *Prevotella intermedia* | 46.47222 | 77.65541 | 0 | 2.67E−06 | 6.01E−04 |
| *Beggiatoa* sp. PS | 46.53704 | 77.60811 | 0 | 2.79E−06 | 6.01E−04 |
| *Crenothrix polyspora* | 48.76852 | 75.97973 | 0 | 4.20E−05 | 5.70E−03 |
| *Clostridium hathewayi* | 49.68519 | 75.31081 | 0 | 1.15E−04 | 1.34E−02 |
| Lachnospiraceae bacterium 5_1_57FAA | 50.10185 | 75.00676 | 0 | 1.78E−04 | 1.91E−02 |
| *Eubacterium ventriosum* | 80.98148 | 52.47297 | 1 | 1.77E−05 | 2.69E−03 |
| *Haemophilus sputorum* | 77.66667 | 54.89189 | 1 | 6.08E−04 | 4.90E−02 |
| 10 mOTU species makers | | | | | |
| *Peptostreptococcus stomatis* | 46.25 | 77.81757 | 0 | 6.56E−08 | 1.80E−05 |
| *Parvimonas micra* | 46.2963 | 77.78378 | 0 | 4.11E−08 | 1.80E−05 |
| *Gemella morbillorum* | 47.93519 | 76.58784 | 0 | 1.57E−06 | 0.000215 |
| *Solobacterium moorei* | 51.22222 | 74.18919 | 0 | 6.31E−05 | 0.004331 |
| unclassified *Fusobacterium* | 54.22222 | 72 | 0 | 0.000176 | 0.00806 |
| Clostridiales bacterium 1_7_47FAA | 51.27778 | 74.14865 | 0 | 0.000365 | 0.013366 |
| motu_linkage_group_624 | 51.01852 | 74.33784 | 0 | 0.000448 | 0.01371 |
| motu_linkage_group_407 | 81.13889 | 52.35811 | 1 | 6.00E−06 | 0.000659 |
| motu_linkage_group_490 | 80.46296 | 52.85135 | 1 | 3.06E−05 | 0.002403 |
| motu_linkage_group_316 | 79.61111 | 53.47297 | 1 | 8.17E−05 | 0.004487 |

TABLE 13

21 MLG species markers identified using the random forest method from 106 MLGs with a gene number over 100.

21 MLG species makers

| | Control rank mean | Case rank mean | Enrichment (1: Control; 0: Case) | P-value | q-value |
|---|---|---|---|---|---|
| *Parvimonas micra* | 38.40741 | 83.54054 | 0 | 3.16E−12 | 2.75E−10 |
| *Fusobacterium nucleatum* | 40.32407 | 82.14189 | 0 | 2.97E−11 | 1.29E−09 |
| *Solobacterium moorei* | 42.2037 | 80.77027 | 0 | 3.85E−09 | 1.12E−07 |
| CRC 2881 | 51.25926 | 74.16216 | 0 | 2.57E−06 | 4.46E−05 |
| *Clostridium hathewayi* | 46.77778 | 77.43243 | 0 | 3.92E−06 | 5.69E−05 |
| CRC 6481 | 52.09259 | 73.55405 | 0 | 1.36E−05 | 0.000107 |
| Clostridiales bacterium 1_7_47FAA | 48.16667 | 76.41892 | 0 | 2.02E−05 | 0.000135 |
| *Clostridium* sp. HGF2 | 48.27778 | 76.33784 | 0 | 2.36E−05 | 0.000147 |
| CRC 4136 | 50.99074 | 74.35811 | 0 | 5.22E−05 | 0.000233 |
| *Bacteroides fragilis* | 49.09259 | 75.74324 | 0 | 5.97E−05 | 0.000236 |
| *Clostridium citroniae* | 51.71296 | 73.83108 | 0 | 0.000861 | 0.001529 |
| Lachnospiraceae bacterium 8_1_57FAA | 51.88889 | 73.7027 | 0 | 0.001024 | 0.001782 |
| *Dorea formicigenerans* | 52.98148 | 72.90541 | 0 | 0.002703 | 0.003409 |
| Con 10180 | 82.03704 | 51.7027 | 1 | 4.87E−06 | 6.05E−05 |
| Con 7958 | 75.27778 | 56.63514 | 1 | 1.36E−05 | 0.000107 |
| butyrate-producing bacterium SS3/4 | 80.57407 | 52.77027 | 1 | 1.98E−05 | 0.000135 |
| *Haemophilus parainfluenzae* | 80.49074 | 52.83108 | 1 | 2.54E−05 | 0.000148 |
| Con 154 | 80.35185 | 52.93243 | 1 | 3.30E−05 | 0.000179 |
| Con 1979 | 79.94444 | 53.22973 | 1 | 5.62E−05 | 0.000233 |
| Con 5770 | 79.39815 | 53.62838 | 1 | 0.000104 | 0.000324 |
| Con 1513 | 76.59259 | 55.67568 | 1 | 0.000701 | 0.001298 |

TABLE 14

164 samples' qPCR abundance and calculated gut healthy index

| sample name(CRC: cases; Con: controls) | 482585 (SEQ ID NO: 10) | 1704941 (SEQ ID NO: 14) | 1696299 (SEQ ID NO: 6), namely rpoB gene | Stage | CRC mini index |
|---|---|---|---|---|---|
| CRC_1 | 0 | 0 | 0.006203293 | 2 | −14.0691259 |
| CRC_2 | 1.86E−05 | 0.087144293 | 0.002625577 | 2 | −2.790341115 |
| CRC_4 | 0 | 0.005819658 | 0 | 2 | −14.07836751 |
| CRC_5 | 0.37491878 | 0 | 0.001675491 | 2 | −7.733973569 |
| CRC_6 | 0.73039561 | 0 | 0 | 2 | −13.37881395 |
| CRC_7 | 0.235418565 | 7.05E−06 | 0.18349339 | 2 | −2.172116584 |
| CRC_8 | 0.429119094 | 0 | 0.018272274 | 2 | −7.368543187 |
| CRC_9 | 9.98E−06 | 0 | 0 | 3 | −15.00028982 |
| CRC_10 | 0 | 0 | 1.60E−06 | 2 | −15.26529334 |
| CRC_11 | 0 | 0 | 1.73E−07 | 3 | −15.58731797 |
| CRC_12 | 0.372006568 | 0 | 0.000316655 | 2 | −7.976287681 |
| CRC_13 | 0.721364334 | 0 | 0 | 2 | −13.38061511 |
| CRC_14 | 0 | 0 | 0.049138581 | 2 | −13.7695258 |
| CRC_15 | 0 | 0 | 0.009579061 | 2 | −14.00622569 |
| CRC_16 | 0 | 0 | 0.000802784 | 4 | −14.36513376 |
| CRC_17 | 0 | 0 | 0 | 2 | −20 |
| CRC_18 | 3.38E−07 | 8.53E−05 | 0.008910363 | 2 | −4.19674629 |
| CRC_19 | 0.000110781 | 5.55E−05 | 0.044982261 | 3 | −3.186066818 |
| CRC_20 | 0.000234301 | 2.89E−05 | 0.066693964 | 2 | −3.115080495 |
| CRC_21 | 0 | 0.006985843 | 0.063669666 | 3 | −7.783949536 |
| CRC_22 | 0.109450466 | 0 | 0 | 2 | −13.65359413 |
| CRC_23 | 0 | 0 | 0 | 3 | −20 |
| CRC_24 | 0.000152828 | 0 | 0 | 2 | −14.60526569 |
| CRC_25 | 0 | 9.72E−05 | 9.80E−06 | 3 | −9.673702553 |
| CRC_26 | 0.002291805 | 0.002622757 | 0.01946802 | 3 | −2.310580833 |
| CRC_27 | 9.35E−05 | 0.001461738 | 0.322093176 | 3 | −2.452112443 |
| CRC_28 | 0 | 0 | 1.61E−05 | 2 | −14.93105804 |
| CRC_29 | 0.000326642 | 7.85E−05 | 0 | 2 | −9.197019439 |
| CRC_30 | 0 | 0 | 0.003779209 | 2 | −14.14086636 |
| CRC_31 | 0.000675175 | 0.000711697 | 0.009892837 | 2 | −2.774322553 |
| CRC_32 | 0.008042167 | 0.000418046 | 0.011960736 | 2 | −2.465214979 |
| CRC_33 | 0.002654305 | 0.023680609 | 0.007125466 | 2 | −2.116281012 |
| CRC_34 | 0.00081495 | 0 | 0 | 1 | −14.36295635 |
| CRC_35 | 0.000571484 | 0 | 0.000169321 | 3 | −9.0047617 |
| CRC_36 | 0.000982742 | 0.0005857 | 0 | 1 | −8.74662842 |
| CRC_37 | 0.000180959 | 6.71E−05 | 0.012612517 | 2 | −3.271631843 |
| CRC_38 | 8.82E−06 | 5.37E−05 | 0 | 3 | −9.774852376 |
| CRC_39 | 0.003822017 | 0.002785496 | 0.000296681 | 4 | −2.833505037 |
| CRC_40 | 0.021036668 | 0.000248796 | 0.014980712 | 3 | −2.368549066 |
| CRC_41 | 0 | 0 | 0 | 1 | −20 |
| CRC_42 | 0 | 0 | 0 | 1 | −20 |
| CRC_43 | 0 | 0 | 0 | 3 | −20 |
| CRC_44 | 0 | 0 | 0 | 3 | −20 |
| CRC_45 | 0.000663002 | 0 | 0 | 3 | −14.39282839 |
| CRC_46 | 0 | 4.92E−06 | 0.013275868 | 4 | −9.061657324 |
| CRC_47 | 0 | 0 | 0.002163301 | 2 | −14.22162768 |
| CRC_48 | 0 | 0 | 2.18E−05 | 2 | −14.88718117 |
| CRC_49 | 0.00571136 | 0 | 9.22E−05 | 2 | −8.759509848 |
| CRC_50 | 0.0002221 | 0 | 9.01E−07 | 3 | −9.89957555 |
| CRC_51 | 0 | 0 | 0 | 3 | −20 |
| CRC_52 | 3.41E−06 | 0 | 0 | 4 | −15.15574854 |
| Con_1 | 2.78E−07 | 0 | 0 | 0 | −15.51865173 |
| Con_2 | 0 | 0 | 0 | 0 | −20 |
| Con_3 | 0 | 0 | 0 | 0 | −20 |
| Con_4 | 0 | 0 | 0 | 0 | −20 |
| Con_5 | 1.71E−06 | 0 | 0 | 0 | −15.25566796 |
| Con_6 | 0 | 0 | 0 | 0 | −20 |
| Con_7 | 0 | 0 | 0 | 0 | −20 |
| Con_8 | 2.34E−06 | 0 | 0.000211515 | 0 | −9.76848099 |
| Con_9 | 0 | 0 | 0 | 0 | −20 |
| Con_10 | 0 | 0 | 0 | 0 | −20 |
| Con_11 | 0 | 0 | 0 | 0 | −20 |
| Con_12 | 8.85E−06 | 0 | 0 | 0 | −15.01768558 |
| Con_13 | 0 | 0 | 0 | 0 | −20 |
| Con_14 | 0 | 0 | 0 | 0 | −20 |
| Con_15 | 0.006715916 | 0 | 0 | 0 | −14.05763158 |
| Con_16 | 0 | 0 | 0 | 0 | −20 |
| Con_17 | 0 | 0 | 0 | 0 | −20 |
| Con_18 | 0 | 0 | 0 | 0 | −20 |
| Con_19 | 0 | 0 | 1.49E−07 | 0 | −15.60893791 |
| Con_20 | 0 | 0 | 0 | 0 | −20 |
| Con_21 | 0.002499751 | 0 | 0 | 0 | −14.20070108 |
| Con_22 | 0 | 0 | 0 | 0 | −20 |

TABLE 14-continued 164 samples' qPCR abundance and calculated gut healthy index

| sample name(CRC: cases; Con: controls) | 482585 (SEQ ID NO: 10) | 1704941 (SEQ ID NO: 14) | 1696299 (SEQ ID NO: 6), namely rpoB gene | Stage | CRC mini index |
|---|---|---|---|---|---|
| Con_23 | 3.37E−05 | 0 | 0 | 0 | −14.82412337 |
| Con_24 | 0.00407976 | 0 | 0 | 0 | −14.12978846 |
| Con_25 | 0 | 0 | 2.11E−05 | 0 | −14.89190585 |
| Con_26 | 0.008105124 | 0 | 0 | 0 | −14.03041345 |
| Con_27 | 2.88E−06 | 0 | 0 | 0 | −15.1802025 |
| Con_28 | 4.91E−05 | 0 | 0 | 0 | −14.7696395 |
| Con_29 | 0 | 0 | 0 | 0 | −20 |
| Con_30 | 0 | 0 | 0 | 0 | −20 |
| Con_31 | 0 | 0 | 0 | 0 | −20 |
| Con_32 | 6.20E−05 | 0 | 0 | 0 | −14.73586944 |
| Con_33 | 0 | 0 | 0 | 0 | −20 |
| Con_34 | 0 | 0 | 0 | 0 | −20 |
| Con_35 | 0 | 0 | 0 | 0 | −20 |
| Con_36 | 0.001536752 | 0 | 0 | 0 | −14.27113207 |
| Con_37 | 0 | 0 | 0 | 0 | −20 |
| Con_38 | 0 | 0 | 0 | 0 | −20 |
| Con_39 | 0.000190886 | 0 | 0 | 0 | −14.57307531 |
| Con_40 | 0 | 0 | 0 | 0 | −20 |
| Con_41 | 1.68E−05 | 0 | 0 | 0 | −14.92489691 |
| Con_42 | 0 | 0 | 0 | 0 | −20 |
| Con_43 | 0 | 0 | 0 | 0 | −20 |
| Con_44 | 0.005333691 | 0 | 0 | 0 | −14.09099072 |
| Con_45 | 0.00045872 | 0 | 0 | 0 | −14.44615077 |
| Con_46 | 0 | 0 | 0 | 0 | −20 |
| Con_47 | 0 | 0 | 0 | 0 | −20 |
| Con_48 | 0.000121349 | 0 | 0 | 0 | −14.6386546 |
| Con_49 | 1.95E−06 | 0 | 0 | 0 | −15.23665513 |
| Con_50 | 0 | 0 | 0 | 0 | −20 |
| Con_51 | 0 | 0 | 0 | 0 | −20 |
| Con_52 | 0 | 0 | 0 | 0 | −20 |
| Con_53 | 0 | 0 | 0 | 0 | −20 |
| Con_54 | 0 | 0 | 1.03E−05 | 0 | −14.99572093 |
| Con_55 | 0 | 0 | 0 | 0 | −20 |
| Con_56 | 0 | 0 | 0 | 0 | −20 |
| Con_57 | 0 | 0 | 0 | 0 | −20 |
| Con_58 | 0 | 0 | 0 | 0 | −20 |
| Con_59 | 0 | 0 | 0 | 0 | −20 |
| Con_60 | 0 | 0 | 0 | 0 | −20 |
| Con_61 | 0 | 0 | 0 | 0 | −20 |
| Con_62 | 0 | 0 | 0 | 0 | −20 |
| Con_63 | 0 | 0 | 0 | 0 | −20 |
| Con_64 | 0 | 2.10E−05 | 0 | 0 | −14.89259357 |
| Con_65 | 0.00096125 | 0 | 0 | 0 | −14.33905455 |
| Con_66 | 0.000280561 | 0 | 0 | 0 | −14.51732423 |
| Con_67 | 0.004437614 | 0.000250648 | 0.00179637 | 0 | −2.899796813 |
| Con_68 | 0.000125259 | 0 | 0 | 0 | −14.63406369 |
| Con_69 | 0 | 0 | 0 | 0 | −20 |
| Con_70 | 0 | 0 | 0 | 0 | −20 |
| Con_71 | 0 | 0 | 0 | 0 | −20 |
| Con_72 | 0 | 0 | 0 | 0 | −20 |
| Con_73 | 0 | 0 | 0 | 0 | −20 |
| Con_74 | 0 | 0 | 0 | 0 | −20 |
| Con_75 | 0 | 0 | 0 | 0 | −20 |
| Con_76 | 1.56E−05 | 0 | 0.000315363 | 0 | −9.436021554 |
| Con_77 | 0.042785033 | 0 | 0 | 0 | −13.78956938 |
| Con_78 | 0.011668395 | 0 | 0 | 0 | −13.97766296 |
| Con_79 | 0 | 0 | 0 | 0 | −20 |
| Con_80 | 0 | 0 | 0 | 0 | −20 |
| Con_81 | 0 | 0 | 1.88E−06 | 0 | −15.24194738 |
| Con_82 | 2.23E−06 | 0 | 0 | 0 | −15.21723171 |
| Con_83 | 0.000446671 | 0 | 0 | 0 | −14.45000408 |
| Con_84 | 1.94E−05 | 0 | 0 | 0 | −14.90406609 |
| Con_85 | 0 | 0 | 0 | 0 | −20 |
| Con_86 | 0.000823554 | 1.02E−06 | 0.000177345 | 0 | −4.2756296 |
| Con_87 | 1.02E−05 | 0 | 0 | 0 | −14.99713328 |
| Con_88 | 0 | 0 | 0 | 0 | −20 |
| Con_89 | 9.38E−07 | 0 | 0 | 0 | −15.34259905 |
| Con_90 | 3.05E−06 | 0 | 0 | 0 | −15.17190005 |
| Con_91 | 0 | 0 | 0 | 0 | −20 |
| Con_92 | 0 | 0 | 0 | 0 | −20 |
| Con_93 | 0 | 0 | 0 | 0 | −20 |
| Con_94 | 0 | 0 | 0 | 0 | −20 |
| Con_95 | 4.75E−07 | 0 | 0 | 0 | −15.44110213 |

TABLE 14-continued

164 samples' qPCR abundance and calculated gut healthy index

| sample name (CRC: cases; Con: controls) | 482585 (SEQ ID NO: 10) | 1704941 (SEQ ID NO: 14) | 1696299 (SEQ ID NO: 6), namely rpoB gene | Stage | CRC mini index |
|---|---|---|---|---|---|
| Con_96 | 2.15E−06 | 0 | 0 | 0 | −15.22252051 |
| Con_97 | 0 | 0 | 0 | 0 | −20 |
| Con_98 | 0 | 0 | 0 | 0 | −20 |
| Con_99 | 2.93E−06 | 0 | 0 | 0 | −15.17771079 |
| Con_100 | 0.012223913 | 0 | 0 | 0 | −13.97092992 |
| Con_101 | 9.50E−06 | 0 | 0 | 0 | −15.00742546 |
| Con_102 | 0 | 0 | 0 | 0 | −20 |
| Con_103 | 0 | 0 | 0 | 0 | −20 |
| Con_104 | 8.39E−05 | 0 | 0 | 0 | −14.69207935 |
| Con_105 | 0 | 0 | 0 | 0 | −20 |
| Con_106 | 0 | 0.000689816 | 0 | 0 | −14.38708891 |
| Con_107 | 0 | 0 | 0 | 0 | −20 |
| Con_108 | 0 | 0 | 0 | 0 | −20 |
| Con_109 | 0 | 0 | 0 | 0 | −20 |
| Con_110 | 0.000307175 | 0 | 0 | 0 | −14.50420471 |
| Con_111 | 0.024307579 | 0 | 0 | 0 | −13.87141943 |
| Con_112 | 0 | 0 | 0 | 0 | −20 |
| Con_113 | 0 | 0 | 0 | 0 | −20 |

Although explanatory embodiments have been shown and described, it would be appreciated by those skilled in the art that the above embodiments can not be construed to limit the present disclosure, and changes, alternatives, and modifications can be made to the embodiments without departing from the nature, principles and scope of the present disclosure.

---

What is claimed is:

1. A kit for analyzing a gene marker set for predicting the risk of colorectal cancer in a subject, comprising one or more TaqMan oligonucleotides configured to hybridize specifically to a gene marker having the nucleotide sequence of SEQ ID NO: 6, wherein one or more detectable labels are incorporated into the one or more TaqMan oligonucleotides at a 5' end, at a 3' end, and/or at any nucleotide position within the TaqMan oligonucleotides.

2. The kit of claim 1, further comprising one or more TaqMan oligonucleotides configured to specifically hybridize to at least one additional gene marker comprising the nucleotide sequence of SEQ ID NO: 10 or SEQ ID NO: 14, respectively, wherein one or more detectable labels are incorporated into the one or more TaqMan oligonucleotides at a 5' end, at a 3' end, and/or at any nucleotide position within the TaqMan oligonucleotides.

3. The kit of claim 2, wherein the one or more TaqMan oligonucleotides are selected from the group consisting of SEQ ID NO: 32 to SEQ ID NO:40.

4. The kit of claim 2, wherein the kit comprises two or more TaqMan oligonucleotides configured to specifically hybridize to the nucleotide sequences of SEQ ID NO: 10 and SEQ ID NO: 6, respectively.

5. The kit of claim 2, wherein the kit comprises two or more TaqMan oligonucleotides configured to specifically hybridize to the nucleotide sequences of SEQ ID NO: 14 and SEQ ID NO: 6, respectively.

6. The kit of claim 2, wherein the kit comprises three or more TaqMan oligonucleotides configured to specifically hybridize to the nucleotide sequences of SEQ ID NO:6, SEQ ID NO: 10 and SEQ ID NO: 14, respectively.

* * * * *

SEQUENCE LISTING

<160> NUMBER OF SEQ ID NOS: 40

<210> SEQ ID NO 1
<211> LENGTH: 816
<212> TYPE: DNA
<213> ORGANISM: Peptostreptococcus anaerobius 653-L
<220> FEATURE:
<223> OTHER INFORMATION: isolated from gut, Peptostreptococcus anaerobius 653-L

<400> SEQUENCE: 1

```
atggccaaaa cacctatcgt agataagggg tgcttcatat cgaatgatgt taaaaggtca      60
atagttttaa acctatgtga gactaagtca atggatctaa ttgcaagaga acactgtgta     120
tctcctagta gtgttgccag aatacttcgt ttaactgaag ataggagaag aaaaaattat     180
cttcctagga ttctatcaat agacgaattc aagtcagtaa atacagttga tgcgtctatg     240
agtgtaaatt taactgattt agaaggcggt catattttg atatcctggt ggataggagg      300
caaagatacc tctttgagta ctttaattcc tatcccttga aggtcagaaa aagggtagaa     360
tatgtgacta cagacatgta taagccatat attgatcttg ccaagaaggt ctttccaaat     420
gccaatattg tggtagataa attccatata gtacagctct tgacaagaga gctaaacaag     480
ttaaggataa atgagatgaa gaagcttaat accaggtcta gagagtataa aatactgaag     540
agatactgga aaatacccct taggaagaag agagacttaa acagtatata tttttacaag     600
aataggcact ttaaaaatat gaccagttca attgatatat tagactatat gttaaaggaa     660
tttcccaact taaagagagc ctatgatttt tatcaaaact tcctattaag tatatctaat     720
aatgatgtcg ctatgcttga agacattcta aatactagga ctgatgaaat tcccatgtgt     780
```

```
tttaggaaga gtataaaaag ccttaaaaag cttaga                              816

<210> SEQ ID NO 2
<211> LENGTH: 504
<212> TYPE: DNA
<213> ORGANISM: Clostridium symbiosum WAL-14163
<220> FEATURE:
<223> OTHER INFORMATION: isolated from gut, Clostridium symbiosum
      WAL-14163

<400> SEQUENCE: 2
atggttgcac ttgtatggct actgattgaa atgaaatata aaatcagtgt cccatctcca    60
ctgttgctca gcatggttta caaacttttg cttccggcta tgcctgccta tcttctggct   120
aaaatcccct ctgggaaatt aacggccagc ttgagaagaa tgccgatttc tacccatatc   180
atgcttgtat tgatcgtcat gctccgcttt gcgccgactg tgctgcatga atttggagaa   240
gtcagggaag ccatgaaaat tcgtggcttc ttaaaatcgg tcggtaatgt tttgaggcat   300
ccaatggaca cgttggaata cgccattgtt ccgatggtgt tccgctcctt aaagatcgcg   360
gacgagttag cagcttctgc catagtcagg ggaattgaaa gccccctacaa gaaagaaagc   420 tactatgtca gccggatcgc tgcgctggat tactttttga ttgttgtcag cgtgggagct   480
gccgtgtgct gctgtctttt atag                                          504

<210> SEQ ID NO 3
<211> LENGTH: 1305
<212> TYPE: DNA
<213> ORGANISM: Unknown
<220> FEATURE:
<223> OTHER INFORMATION: isolated from gut, unidentified

<400> SEQUENCE: 3
atgttagcaa tcgtaggttt attaactatc ctggtcgtaa tgtttctgat tatgacaaaa    60
aaatgttcga ctctggtcgc actgattgca gttcccatga ttgcatgtgt tattgtgggt   120
cagggcgccg atatgggagg gtacataacg gccggtatca aaagtgtggc cgccaccgga   180
gtcatgttta ttttttgcagt ggccttttcc ggtgtcatgg gtgatgtggg tgcatttgaa   240
atcgtagtga ataaaatact caggattatt gggaaagatc ctttgaaaat ctgtatcggc   300
acgctgatta tcacattgat gacccacctg gacggctccg gcgcaacgac attttgatc   360 acaataccgg cgctgctgcc gatatacgat aaattgaaga tggatcggcg tgtgctggca   420
actatagtgg cggcaggagc aggaaccatg aatctcgtcc cttggggagg gccgacgatc   480
cgagcagcga cggcactgga ggtctcactg accgagcttt acaatcctat gattgtccct   540
cagctttgcg gagtcgccgc ctgcgtgaca gtggcggtga tgtttggcct gaaggaacgg   600
aaacgtttaa aagggactct ggaatctgtt tcggtagagc ctccgaaatt tgaggactta   660
ccggaggagg agagagtgaa acgccgtccc caccttgtct ggtttaacat tctgctcatt   720
atagttacaa ttgtgtcatt ggttatggag cttttgccgc cggccggctg ttttatggcg   780
gcgctgtgca tcgcaatgct ggttaactac cgtgatttaa aggatcaggg aaaacggatg   840
gacgagcatg cggtagcggc catgatgatg gcatccaccc tgtttggcgc aggctgcttt   900
accggtatcc tgggaggctg cggcatgctg gaagcgatgg cccagggact ctgtgatatt   960
ctcccggtag ccattatggg tcacattgcg attttggtgg cagttttctc catgcctctg  1020
tcgctgatgt tcgatccgga cagcttctac tatgcagtac ttccggtaat tgcagtggcg  1080
gccgaggtgg ccggtgttcc ggcattggca gtggccgcg cggcgatatg cggacagatt  1140
```

```
actgttggat tccccatttc accactgact ccatccacct tccttctgac aggactaacg    1200
ggcgtggatc tcggggacca tcagaagcac agtttcgtgt ggctgtggct gatttccctg    1260
acgattgtgc tggttgccgt ggtgatgggc gtaattccgg tatag                    1305

<210> SEQ ID NO 4
<211> LENGTH: 1401
<212> TYPE: DNA
<213> ORGANISM: Faecalibacterium prausnitzii L2-6
<220> FEATURE:
<223> OTHER INFORMATION: isolated from gut, Faecalibacterium prausnitzii
      L2-6

<400> SEQUENCE: 4
atgccgaacg aacgacatta ctccaatgaa ctgaatctgg aaagcgtggg catcaatctg     60
ccctacaaca tgcaggccga gcagagcgtg ctgggtgcgg tgctgctcaa gccgaaaaca    120
ctgaccgacc tggttgagat catccggccg gaaatgttct acacccggca gaacgcccaa    180
atttattcgg aaatgctccg gctgttcacc agcgaccaga ccattgattt cgtcaccctg    240
ctggacgcgg tcatctcaga cggcgtgttt cccagcgcgg acgaggcgaa agtctacctg    300
accggtctgg ccgagacggt gcccagcatc tccaacgtga agcctacgc ccagatcgtg    360 caggaaaaat atctggtccg ccagctcatg ggtgtggcga agatatctt gcaggatgcg    420 ggcgacgagc cggacgcgga cctgctgctg gaaaacgccg agcagcgcat ttatgagatc    480
cgctccgggc gggattccag cgccctgacg ccccttctt ccagcatggt ggaaacgctg    540
accaatctgc agaagatcag cggcccggat gccgataagt acaagggcat ccctacaggc    600
ttccgcctgc tggacaccgt gctcaccggc cttggccgcg cgaccttat tattctggct    660 gcccgccccg gtatgggcaa gaccagtttt cgctgaaca ttgccacccg cgtggccatg    720
cagcagaaag taccggtggc catcttcagc ctcgaaatga ccaaggagca gctgaccaac    780
cggatcctct cggcggaggc cggcatcgac agccaggcgt tccgcaccgg cgccctccgg    840
gcggaggact gggagtacct ggcccttgcc accgagaagc tccatgacgc gcccatttat    900
atggatgaca cctcgggcat caccatcacc gagatgaaag ccaagatccg ccgggtgaac    960
caggacccca gccgcccccaa tgtggggctc atcgtcatcg actatctgca gctgatgacc    1020
acgggccagc gcaccgagaa ccgtgtacag gagatcagct ccatcacccg aaacctcaag    1080
atcatggcca aagagatgaa tgtgcccatc attgcgctga ccagctgtc ccgtgcggtg    1140 gaaaagcagg gcaacaactc ctcccaccgc ccccagctgt ccgacctgcg tgattccggt    1200
tccatcgagc aggacgccga ctgcgtgctg ttcctctacc gtgattctta ttacgccagc    1260
cagaacccgg acggtgccga ggtggacgcc gacacggccg agtgcatcgt ggccaaaaac    1320
cgccacggtg agaccagtac cgtgccgctg ggctgggatg tgcccacac ccgctttatg    1380 gatgtggact tcaaacgctg a                                              1401

<210> SEQ ID NO 5
<211> LENGTH: 858
<212> TYPE: DNA
<213> ORGANISM: Faecalibacterium cf. prausnitzii KLE1255
<220> FEATURE:
<223> OTHER INFORMATION: isolated from gut, Faecalibacterium cf.
      prausnitzii KLE1255

<400> SEQUENCE: 5
atctccaaac tggaaaaaac gctgcgggca cggttcccga aaacgcagca gggcgaactg     60
ctggccgggg cggtgctggc cttctgcctg ccggtgggca cctttctgct cacaagcgcc    120
```

```
gtgtgccttc tggcggcaaa aatcagcccc tggctcggcc ttgccgtgca gatgttctgg    180
tgcgggcagg cgctggcggc aaagggactt gtgcaggaga gccggaacgt ttacaacaag    240
ctggtaaagc ccgacctgcc cgccgcccgc aaggccgtga ccgcatcgt ggggcgggac     300 accgagaacc tgaccgccga gggcgtgacc aaggctgccg tggagactgt ggccgagaat    360
gccagcgacg gcgtgattgc gccgctgctg tacatgctgc tgggcggcgc gccgctggcg    420
ctgacctaca aggccgtcaa caccatggac agcatggtgg gctacaaaaa cgagacctat    480
ctctacttcg gccgggcggc ggcaaagctg gacgatatgg caaactacat tcccagccgc    540
cttgccgccc tgctgtgggc ggcggctgct gccctgaccg gcaacgatgc caaaggcgcg    600
tggcgcatct ggcggcggga ccggcgcaat cacgccagcc ccaacagcgc ccagaccgaa    660
agcgcctgcg ccggtgcgct gggcgtgcag ctggccgggc cggcctacta ctttggcgaa    720
tactacccga aacccaccat cggcgatgcc ctgcgcccca ttgagccgca ggacatcctg    780 cggggccgacc gcatgatgta cgccgccagc attctggcgc tggtgctcgg gcttgtgata    840 cggggggttcg ttgtatga                                                 858
```

```
<210> SEQ ID NO 6
<211> LENGTH: 930
<212> TYPE: DNA
<213> ORGANISM: Parvimonas micra ATCC 33270
<220> FEATURE:
<223> OTHER INFORMATION: isolated from gut, Parvimonas micra ATCC 33270

<400> SEQUENCE: 6
aatcaattta gaattggttt atcaagaatg gagagagttg ttagagaaag aatgtcaact     60
caagatccag accttgctac gcctcaagga cttattaata taagacctct tgttgcgtct    120
ttaaaagaat tcttcggttc ttcacaatta tcacaattca tggatcaaaa caatccactt    180
gcagaactta ctcataagag aagattatca gcattaggac ctggtggtct tagtagagat    240
agagcaggat acgaagtaag agacgttcat gaaagtcact acggaagaat ttgtccgata    300
gaaactccag aaggtccaaa catcggtctt attacttctc ttacaactta tgcaagagtt    360
gatcaatatg gatttattga acaccatat cgtgttgtaa ataatggaat tgctacaaag    420
gacattgttt atttaactgc tgatgaagaa gatgaagtta ttatcgctca agccaatgaa    480
ccacttgatg aaaatggacg ttttgtaaac gaaagagtaa gtggtcgtgg tattaatggc    540
gaaaatgata tttatccaag agatacaatt caacttatgg acgtttctcc tcaacaaatt    600
gtatcagttg gtacagcaat gattcctttc cttgaaaatg acgatgctac tcgtgcgttg    660
atgggttcaa acatgcaaag acaagcagtg cctctacttg ttactgaagc tcctattgta    720
ggaaccggta tagaacataa agcggcaaga gatagtggtg ttgttatcat tgctaaaaat    780
tcaggaattg ttacaaaagt tgatagtgat gaaattcata ttaaaagaga tttagataat    840
gtagttgata aatatagatt acttaaattt aaacgttcaa atcaaggaac aacaattaat    900
caaagaccta tagttaatga aaatgacaga                                      930
```

```
<210> SEQ ID NO 7
<211> LENGTH: 336
<212> TYPE: DNA
<213> ORGANISM: Coprobacillus sp. 8_2_54BFAA
<220> FEATURE:
<223> OTHER INFORMATION: isolated from gut, Coprobacillus sp. 8_2_54BFAA

<400> SEQUENCE: 7
```

```
atggcgattg atactgaatt agcaaaaaga ttacgttcat atcgtaattt taaacattta      60
acacaaaaag atgttgctgc gcatttaaat gttcctcatt ctgcaatttc cgatatagaa     120
aatggtaaaa gagacattac tgttagcgag ttaaaagtgt tttcaaattt atatggtaga    180
agtgtagaaa aaattatgag cgggaaaaaa tatgactatt ataatattgc caatatcgct    240
cgtttactta ctgaacttcc tgatgatgat ttaaaagaaa tcatgtttat tattgaatat    300
aaaagaaaaa gaaatgaaga acgtcatttg aaataa                              336
```

<210> SEQ ID NO 8
<211> LENGTH: 594
<212> TYPE: DNA
<213> ORGANISM: Unknown
<220> FEATURE:
<223> OTHER INFORMATION: isolated from gut, unidentified

<400> SEQUENCE: 8

```
atggcaatgc tcactgtaga aaatatcaat gtatattacg gcgtgatcca cgcccttaaa     60
gacatctcct ttcaggtaaa cgaaggcgag atcgtcgcac tgatcggcgc aaacggtgcc    120
ggcaaaacca ccaccctgca gactgtcagc ggcatgctga gcgcaaagtc cggttcgatc    180
cgatttcagg atcaggagat ttccagaatg ccggagcaca aaatcgtgaa gcagggaatt    240
tcccacgtcc ccgaaggacg ccggatgttc tccaatctga cggttttgga aaacctgaaa    300
atgggcgctt acaccagaaa agacaagcag gaaatcaaca attccctgga atggtttat    360 gagcggtttc cccgcttaaa ggaacgtacc cgccagctgg caggaactct tccggcggt    420 gaacagcaga tgcttgcaat gggacgtgca ctgatgtctc atccgaagat catccttctg    480
gatgaaccgt ctatgggact ttcaccgatt tttgtaaatg agattttcga aattatcaag    540
aaagtcagtg cagccggcac gaccgtactt ctggtagagc agaatgcaaa gaaa          594
```

<210> SEQ ID NO 9
<211> LENGTH: 432
<212> TYPE: DNA
<213> ORGANISM: Peptostreptococcus anaerobius 653-L
<220> FEATURE:
<223> OTHER INFORMATION: isolated from gut, Peptostreptococcus
      anaerobius 653-L

<400> SEQUENCE: 9

```
tatttttaca agaataggca ctttaaaaat atgaccagtt cagttgatat attagattat     60
atgttaaaag aatttcccaa cttaaaagat gcctatgatt tttatcaaaa cttcctatta    120
agtatatcta ataatgatgt ggctatgctt gaagatattc taaatactag gactgataaa    180
ataccaatgt gttttaggaa gagtataaaa agccttaaaa agtttagaaa gtatgtggta    240
aattcactga aatatgacta tacgaatgcc atggtggagg gtaaaaacaa caagataaag    300
gtaattaaaa gagtatccta cggatatagg agttttagga atttttaaggc aaggataatg    360 ctaatggaaa ggtataaaat acaaagggc aacatccata gttatcagtt tgctatggat    420
gctgccgcat aa                                                         432
```

<210> SEQ ID NO 10
<211> LENGTH: 1935
<212> TYPE: DNA
<213> ORGANISM: Unknown
<220> FEATURE:
<223> OTHER INFORMATION: isolated from gut, unidentified

<400> SEQUENCE: 10

```
aatatccgat atggcaacgg agctctggta gtagtccggg caagggaaaa ccttgtacat      60
ggcgaagcag agcagattac cttcaatact aaaatattag aaaggtgcgt gaggcatttg     120
agaaatccga ttgaagtatt gaaaactcta caagagaaag caggcaacga aactatcaa     180 tttgaacgcc tgtaccgaaa tctgtacaac gaggagtttt tcctattggc atacggaaat     240
ctctctgcaa aagagggaaa tctgaccaag gaacagacg gcgccacaat agacggaatg     300
ggaatggagc ggattcgcaa gctgattgaa agcctgcgga accacagtta ccagccgtcc     360
cctgcgagac gtgcctatat cccaaaatct aatggaaaac ggcgtccgtt aggcataccc     420
tctgttgacg ataagctggt gcaggaagtt gtgaggttaa ttctcgaaag tgtgtatgaa     480
agcaattttt ctgaacattc gcatggtttt agaccgaaca ggagctgtca cacggcactg     540
acccagattc aaagaaactt cacaggggtt aaatggttca ttgaggggga catcaaaggt     600
tattttgaca ccatcgacca ccatatcctt gtggatattt taagaaggcg cataaaggac     660
gaatacctaa tctcgctgat atggaaattt ctgaaagccg atacttaga agactggaaa     720 ttcaatccta cctattccgg cactccgcaa ggctcggtca tcagtccaat acttgccaat     780
atctacctta acgaattcga tacctatgtt gaagaataca tagagaaatt caaccgtggt     840
aaaagacgtg aaagaaacag tgagtatcgc ttttatagtg atggcgcatc gaaactgagg     900
gtaaagtacc gcgggttatg ggaaataatg acagccgatg aaaaagaaaa agccaaatgt     960
gaagtaaatg agctcatgaa aaagcaaaa cagattccag ctatgaatcc gatggacagc    1020
aattaccgcc gtctgctcta ttgcaggtat gcggatgatt ttatttgcgg agtaatcgga    1080
agcaaggaag atgcagaaac catcaaggct gattttagcc ggtacctgaa agaaaagctg    1140
ggactggata tgtcggaaga aaagacactg attacacact caaacgaaaa agcggcgttc    1200
cttggctacg aaatcgctgt ttccagaagc aatgaataca aaaagataag caacggacag    1260
aaggcaagaa cctttaatgg gcgtgttcat ctatttatgc cacataataa atgggttaag    1320
aagctgacca gttgcggagc aatggaaatc aaacagcagg acggcaaaga aatatggaaa    1380
ccgcaggcga ggaaagacct catcaacaaa gagccgattg aaatcctaag catttacaat    1440
gccgaaattc gtgggctgta caattattat tgtttggcaa gcaacgtatg caagctgcag    1500
aaatattact acatcatgga atacagcatg taccagacgt ttgcagcgaa gtaccgtgat    1560
aatttgcgga aaacgattaa caagcatacc cgaaacggcg tgtttggtgt cagctacact    1620
acaaaaaccg gcaacgagaa acgggcgaca ttcgtgaaag gaagcttcca aaaacggact    1680
gtcagcttag attacagtga tgaaatcccc tcttatcctg ccgcaaaata tagtcggaaa    1740
aacggcttaa ttgagcggtt acagggtgga aaatgtgaac tatgcggaca gcagaccgac    1800
aatgtaaaag ttcatcatgt caggaagctg aaagaattag ccggtatgaa agaatgggaa    1860
agaaaaatgg ttcagatgaa cagaaaaact ctggttgttt gtaatacatg ttatggaaac    1920
ataacaggca agtaa                                                    1935
```

<210> SEQ ID NO 11
<211> LENGTH: 1062
<212> TYPE: DNA
<213> ORGANISM: Roseburia intestinalis L1-82
<220> FEATURE:
<223> OTHER INFORMATION: isolated from gut, Roseburia intestinalis L1-82

<400> SEQUENCE: 11

```
atggaaaaag taaaggcatt ttgtaaacgg aaaaacattg agatatccgt caagcgctac      60
ctgattgatg cacttggtgc gatggcacag ggattatttg catcgctttt gatcggaacg     120
```

```
atcatcagta cacttggaac gcagcttaat attccgattc ttgtgacagt cgggacttac    180
gcgaaagcgg cagtcggacc ggcaatggcg atcgcaatcg gatatgcact gcaggcagcg    240
cctttagtac tgttttcact tgcggcagtc ggtgcggcgg caaatgaact tggcggggca    300
ggcggaccgc ttgcggtact tgtggttgca attttttgcag cagaatttgg aaaagcagtt    360
tccaaagaga caaaaatcga tattattgtc actccgtttg tgaccatttt tgtcggggtc    420
gcgctttcta tctggtgggc tccggcgatc ggtgcgcag cgagtgcagt cggtaatgcg    480
atcatgtggg caaccgagct gcagccgttt tcatgggaa tcattgtatc tgtgatcgtc    540
gggattgcac tgacactgcc gatcagcagc gcagcaatct gtgcagcact tggactgacc    600
ggattagccg gtggtgcagc acttgccgga tgctgtgcgc agatggtcgg atttgcagtg    660
gcaagtttcc gtgaaaataa atggggcgga ttgtttgcac agggaatcgg tacatccatg    720
cttcagatgg gtaatatcgt gaaaaatccg cgcatctggc tgccggcgac attggcgtct    780
gcaatcaccg gaccgatcgc aatgtgtctg ttccatttac agatgaatgg tgcagcagtt    840
tcctccggta tgggaacctg tggactggtc ggacagattg gtgtctatac gggatggatc    900
gcagatattg aagcgggaag caaagctgcc attacaccga tggactggat cggactgatt    960
ttcgtaagct ttcttctgcc gggcgtttta tcatggcttt ttagtgtgtt attccgtaag   1020
atcggctgga tcaaagaagg cgatatgagg ctggacttat aa                      1062

<210> SEQ ID NO 12
<211> LENGTH: 873
<212> TYPE: DNA
<213> ORGANISM: Unknown
<220> FEATURE:
<223> OTHER INFORMATION: isolated from gut, unidentified

<400> SEQUENCE: 12
atgaaacgta tttattaac tggagcaagt ggatttatag gtaaaaacat taaagagaca     60
ttaaacagta aatatgacat atggagcccg tcaagccagg agctggattt aaaagatacc    120
gaatgcgttg aagcatattt gaagcagcat tctttcgatg taatattgca tgcagcaaat    180
tgtaatgata caaggaattc catatcagca tacgatgtac tcaatggaaa tctcagaatg    240
ttttttaacc tagagagatg ttctcactat tatggaaaaa tgatttattt tgggtctggg    300
gcagaatatg acagaagtaa taacatccct aatatgtcag aggactattt tgataccagt    360
gttccgaaag atgcttacgg actttcaaaa tatattatgg caaaagcctg tttaaatcag    420
aagaacattt atgaattgtg tttatttgga gtatacggaa aatatgagga atgggagaga    480
agatttatct ctaatgcgat atgtcgtgca ttaaagggta tggatattac gcttcataaa    540
aatgtatact ttgattattt gtgggtagat gacctcataa aaattatttc ttttttcatt    600
gagaaagata acttgaggta caagaggtac aatgtgtgta gaggcgagaa ggttgatcta    660
tattcgctgg cagtacaggt aaagaagact ttggatagcg aatgttcaat attagttggt    720
gagcctggat ggaagaggga gtatactgcg ataacaata gaatgttgaa cgaaatgaat    780
ggtttatctt ttacaaaact ggaagtgacg atagctgaat tgtgtgaata ttataaagag    840
catttatcag aaatagttac tgaaaaattg taa                                 873

<210> SEQ ID NO 13
<211> LENGTH: 777
<212> TYPE: DNA
<213> ORGANISM: Unknown
<220> FEATURE:
```

<223> OTHER INFORMATION: isolated from gut, unidentified

<400> SEQUENCE: 13

| | |
|---|---|
| atgaagaata tgataaaaat atttgaaaat gacgaattcg gaaaagtgag aacagtcatt | 60 |
| aaggacggcg aaccgtggct tgtaggaaaa gatgttgcgg aaattttagg gtattccaac | 120 |
| acaagggacg ctctttcacg tcatgtggat accgaggata aaaccaccgt cgtgatttcc | 180 |
| gacagtggtt caaattacaa gagcaagacc actattatca atgaaagcgg cttttacagc | 240 |
| ttagttctct caagcaaaat gccgagagcc aaagagttca ggcgttgggt gaccgccgaa | 300 |
| gtcctcccca ccatcagacg caccggcggc tacgttttcca acgaggatat gttcatcaaa | 360 |
| aactatctcc cctttctcga cgagccatac cgtgacctgt tccgacttca aatgaccatt | 420 |
| atcaacaagc tgaatgaacg tatccgccac gatcagccgc tggtggagtt tgcgaatcag | 480 |
| gtgtcaaata ccgataatct tatcgacatg aacgcaatgg caaagcttgc gagagcggaa | 540 |
| aatatccccg tcggcagaaa caagctttac ggctggctga aggaaaagg tgtgcttatg | 600 |
| gcaaacaatc tgccgtatca ggcttttatc gaccgcggat attttccgt aaaggagtcg | 660 |
| gtgtttgaaa ctgcgactat gacaaagact tatcagcaga cgtttgttac gggcagggg | 720 |
| cagcagttcg tcataaattt gctgaagaaa tattatggga aggaggtttt gcaataa | 777 |

<210> SEQ ID NO 14
<211> LENGTH: 687
<212> TYPE: DNA
<213> ORGANISM: Fusobacterium nucleatum vincentii ATCC 49256
<220> FEATURE:
<223> OTHER INFORMATION: isolated from gut, Fusobacterium nucleatum
      vincentii ATCC 49256

<400> SEQUENCE: 14

| | |
|---|---|
| tctgcaaaag aaaaagttgc tgcattagtt gctgcattaa aagcagatgg atatgatttt | 60 |
| actgttggta tccctcttga tacaccaata ggaaaatctg aaagagttgt aagtgctggt | 120 |
| aaagggattg gagataaaaa gaatatgaag ctaattgaaa acttagcaaa acaagctgga | 180 |
| gcttctattg gttcttctcg tccagtggca gaaacattgc aatatgtacc tcttgaccgt | 240 |
| tatgtaggaa tgtcaggaca aaaatttgtt ggaaaccttt atatagcttg tggaatttca | 300 |
| ggagctttac aacatttaaa aggaattaaa gatgcaacaa caatagttgc tataaataca | 360 |
| aactcaaatg ctccaatatt taagaatgca gactatggaa tagttggaga tttagcagaa | 420 |
| atttaccctt tattaactaa ggaattagat aatggagaag ctaaaaaaga tgcaccacct | 480 |
| atgaagaaaa tgaagagagt tatacctaga gtagtgtata gtcctcatgt atatgtatgt | 540 |
| agtggttgtg gacatgaata caatcctgat ttaggagatg aagattctga cataaaacca | 600 |
| ggaactagat ttaagatttt accagaagat tggacttgtc ctgattgtgg agatccaaaa | 660 |
| tctggatata tagatgcaaa aaaataa | 687 |

<210> SEQ ID NO 15
<211> LENGTH: 1206
<212> TYPE: DNA
<213> ORGANISM: Unknown
<220> FEATURE:
<223> OTHER INFORMATION: isolated from gut, unidentified

<400> SEQUENCE: 15

| | |
|---|---|
| atgaggttat tttttgatat ggtatgtaac ggcagggcat tgcaaaatgt acaaatgtat | 60 |
| aaattgaata tggtttttaga tgtacacccc tatgctatta cagcaccgtc aaaaactggt | 120 |

-continued

```
ggccgttggc agacatatgt aaaggaaggt gataagcgta agattataag ggcttcttca    180
aaggaaaaac taatggacaa attatatact gcctattttg ttcaaaatgg tgtttctggt    240
atgaccatgg acaagctttt tctcgaatgg ttagcttata aggaatgtat cacaaatagt    300
atgaatacga ttcgcagaca tgaacaacac tggaaaaagt attttcagga tatttcccca    360
aataaggtat cttcctatga tcgtctggaa ttgcagaaag aatgtaatca gttaataaaa    420
gttaataacc tttcttccaa agaatggcag aatgtaaaaa caattctttt aggtatgttt    480
gactatgcct ttgaaaaagg atatattaat acaaacccca tgcccagtat aaaatcact     540
gttaaattcc gtcaggtcaa taaaaagagt ggtaggactg aaacatatca gacagacgaa    600
tacaaagcac ttatgcaata tctagatgca gaatatacag ctacagaaga ccttgcttta    660
ttggctgtta aatttgattt ttttattgga tgccgtgttg ctgagttggt agctctcaag    720
tggtgtgatg ttgaaaatct acggcattta catatttgta gggaagaggt taaagagtct    780
gtccgtgttg gtgatacctg gaaagatgtt tataccgttt cagagcatac taagacatat    840
acagaccggt ctataaaattt agttcctaat gcgattgcta ttttaaatca tatccgtctt   900
aaaatggctt ataatgtatc tgacgatgat tatatcttta cccggaacgg ttcccggatc    960
acttcacgcc agattaatta tattcttgaa aaagcatgta caaaactggg aattatgatt   1020
aagaggtcgc ataaggtaag aaaaacggtt gcaagtcgtc tcaatgtcgg tgaggttccg   1080
ttagattcta ttcgtgagct gttaggtcat gcaaatttaa gcactacact aagttatatt   1140
tataatccgt tatcggaaaa agaaacctat aacctgatgt ccagagcctt ggggaaagtt   1200
caatag                                                              1206
```

<210> SEQ ID NO 16
<211> LENGTH: 945
<212> TYPE: DNA
<213> ORGANISM: Faecalibacterium prausnitzii L2-6
<220> FEATURE:
<223> OTHER INFORMATION: isolated from gut, Faecalibacterium prausnitzii L2-6

<400> SEQUENCE: 16

```
atgaacagag aaacggtgaa catggtgcgc agtccgattt ctgtggaggg gaacatccgg     60
cttgttccgt attatccggc ctacgataca gcacttgcgt ggtatcagga tgcacagctc    120
tgcaaacagg tagataacag ggacttcgtt tatgatttgc cgctgctgaa gcggatgtat    180
cattatctgg acacacacgg ggaactgttt tatattgagt atcggggtgt gctttgtggt    240
gacgtcagcc tgcggacgac cggcgagctg gccatcgtca tctgcaagga gtaccagaat    300
aaacacatcg gcggaaggt catcgaaaaa atgctggagc tggctcggga aggggcttg     360
gcggagtgct tcgcgcacat ctattctttc aatacccagt gcagaaaat gtttgaatcc    420
attggctttg tcccacagga cgaagaacgc tatatctaca aattgcaaaa aggagaaccg    480
actatgacaa aactgactct ggaagaaaag caggagctca tccggatggc ccttgcggcc    540
agggagaggg cttacgtgcc ttacagcgac tttatggtgg gcgctgccct gcgcgccgag    600
gatggccgtg tctttaccgg ctgccatgtg gagaatgccg cctttacccc caccagctgc    660
gccgagcgca ccgcgctgtt caaagccgtg agcgagggcg tgaccaaatt tacggacatc    720
gccgtggtag ctcccgccg gggcgagatc aatcagcaga tcacctcgcc ctgcggcgtc    780
tgccgtcagg cactgtttga gtttggcgg ccggagctga acgtcatcat ggccaaaacg    840
ccggatgatt tcatggagcg cagcatggat gagctgctgc cctttggctt cggtccctcc    900
```
aatgtggcgg gcaacaaggc cgtggaagag gaagaaaaag gctga        945

<210> SEQ ID NO 17
<211> LENGTH: 627
<212> TYPE: DNA
<213> ORGANISM: Clostridium hathewayi DSM 13479
<220> FEATURE:
<223> OTHER INFORMATION: isolated from gut, Clostridium hathewayi DSM
      13479

<400> SEQUENCE: 17
atgcctatac ttcagcagct tctcacatta gtagagcagc acttcggtaa caaatgcgaa        60
atcgtgcttc atgatctgac aaaggattac aaccatacca ttgtcgatat ccgaaacgga       120
gacattaccc atcgttccat cggggggctgc ggaagcaact tagggctgga agtcctgcgc      180
ggaaccgtgc tggatgggga tcgttttaac tatgttacca ccacacagga cggaaagatt       240
ctccgttcct catcgatcta tctaaaaaat gatcagggcg aggtcatcgg atcgatctgc       300
gtgaacctgg atatcacaga gacacttcag tttgaagggt atttacgcca gtttaaccag       360
tttgacagct ttacttccaa cgacgaggag atttttcgctc ccgacgtgaa taatcttctc      420
agccatctga ttcagatggg acaggaacag atcggaaagc ctgcgctgga gatgaacaag      480
aacgagaaga ttgagtttat ccgtttcctt gaccagaaag gagcattcct catcacgaag       540
tccggggaac agatctgtga acttctggga atcagcaaat ttacctttta taattacctt      600
gaaagcagcc gcagccagtc ggattcg                                            627

<210> SEQ ID NO 18
<211> LENGTH: 708
<212> TYPE: DNA
<213> ORGANISM: Eubacterium ventriosum ATCC 27560
<220> FEATURE:
<223> OTHER INFORMATION: isolated from gut, Eubacterium ventriosum ATCC
      27560

<400> SEQUENCE: 18
gcagcttcaa actacgacct tgtacaaca atccttagaa atgaatgggg atacgatggt        60
atcgtaatga ctgactggtg ggccaagatg aacgacgttg tagaaggtgg cgaagaatca      120
aatcaggata caagagatat ggttcgctca cagaacgacg tatatatggt tgtaaacaat      180
aacggcgcag aagttaactc aaacaacgac aacacagaga aatcaattaa agagggaaga      240
cttacaatcg gagaacttca gcgagctgca atcaacatct gcaacttcat tctttcagca      300
cctgttattg aaagagaatt agttgacaca acgttgcaa acattacga ttcagttcca        360 aatgatcagg ccaagtatga agtatttaac attgaaaaag acaataaggt aatgttcaat      420
agcggagcag aagcaacatt ggaagttgaa gacgaagggg aatacacaat tattgttaac      480
atctcatttg acaagtccaa cttatcacag tcaacagtaa acgttaatgc caacggcaca      540
acaatggtag taatccagac taatggaaca gacggcaact ggattacaca gaagctttgc      600
aaggttaaac ttgacaaggg tgtatacaac ttaaaacttg aagaagtatt agcaggaatc      660
aaagttaaat atattcagtt taagaagatt cctaagaaaa ataaataa                    708

<210> SEQ ID NO 19
<211> LENGTH: 1161
<212> TYPE: DNA
<213> ORGANISM: Bacteroides clarus YIT 12056
<220> FEATURE:
<223> OTHER INFORMATION: isolated from gut, Bacteroides clarus YIT 12056

<400> SEQUENCE: 19

-continued

```
atgaaaatca aacaattagc gaaaagcgca tcattcttgc tggtggcagg ttttatcagt      60
tttactattc cgtcgtgtag cagtgaagaa gaaatcatca tccttcagga tgtaaaagta     120
aacagtgaaa gcttcaatct ggccgaagac ggcagtacga ccatagaagt caaggtagta     180
cccgaaaata ctccaatagc caaagccgta ctcagcacat cattatttaa tgaaagcggt     240
gttttcgaag taacccgact cactcccaaa ggtaacggtg tatggcagat agcagcaaaa     300
gtaaaggact tctcacgcat tcaaaacggt caggacgtaa tactttccgt ctatcaggaa     360
gataatatgt atatccaaac cacattgaaa ataaacgacc catatagcat cgagggtaaa     420
tatacaccgg tccatccgca agcctttact ttctacagtg ccgaagacgg caaactgatg     480
gagattccgt tcatcatcac agccgacaac gcagccgacc ttgccgccat cagctacgac     540
aatataaagg tagtcaatgg caccggaagc tctacaccca gcataagtat cacacatttc     600
gcaatagctc cgatgacagg taaaacaggc ttctatctgc aagtggataa cgcccaactc     660
gaaacggtaa aaaagccat cacaaccatc gcttttttgg actgccgggt tatgataacc     720
ggccctaacg gccgtgttgc ctatactcct gtgcgcctca ttgtttcttc tccgaagtgc     780
atcatcaagg acgaccaact cagcctgctg catacagaat tgtccgcccc ggagtttaat     840
agacaaatca ccatagatat gacccacgat ttttatcgtt tgggcaaaca gaatgataaa     900
acaacctttg aggcgtttga aaaccgaggc ttgtataact cacaaggaga aatggcagat     960
gcagaccctc agttcatttc gttgggttat accactcagg gcaaaaatac aacatgtaac    1020
gtaactttaa aacatgatgc cacaattcct gcaatcggca cttaccacat ggtagaacgc    1080
ctaaaaggat attgggaata tgacggaaag aaatatccga ccgtttgtac agacctgcaa    1140
ttccaaatca cgattaaata a                                             1161
```

<210> SEQ ID NO 20
<211> LENGTH: 750
<212> TYPE: DNA
<213> ORGANISM: Coprococcus catus GD/7
<220> FEATURE:
<223> OTHER INFORMATION: isolated from gut, Coprococcus catus GD/7

<400> SEQUENCE: 20

```
atgaaaggaa aaagagttat tgcaggcatt ctgcttgcag gaattttagc agttaccctg      60
gcagggtgta aaacacacaga taacactaaa gaagaatcag aaaagccggt tattaccctc     120
ggcagcgata gctatccacc atacaattat ctgaatgagg atggtgtacc gacgggcata     180
gatgtggaac tagctacaga agcttttcaaa agaatgggat atcaggtgaa tgtcgtccaa     240
atcaactggg aggagaaaaa agaactggta gagagtggaa agatcgattg tatcatgggt     300 tgttttttcta tggaaggacg tcttgacgat taccgctggg caggggcgta catagcaagc     360
cgtcaggttg tagcggtaaa tgaggacagt gatatttata aattgagtga ccttgaggga     420
aagaacctgg ctgtccagtc cacaactaaa ccggaagtta tatttctgaa ccggttggat     480
aagagaatcc acaaactggg aaatctgatc agtcttggac accgcgagct gatatataca     540
tttcttggga aaggatatgt agatgcagtt gccgcacatg aggaatcaat catccagtat     600
atgaaggatt atgacataga cttccgtatc ctggaagaat cgctgatgat tacggggata     660
ggtgttgctt tcgcaaaaga tgatgacaga ggaattgtga gcagatggac cagacccttg     720
aagaaatgcg taaggatggc acgtctttga                                      750
```

<210> SEQ ID NO 21

```
<211> LENGTH: 696
<212> TYPE: DNA
<213> ORGANISM: Burkholderiales bacterium 1_1_47
<220> FEATURE:
<223> OTHER INFORMATION: isolated from gut, Burkholderiales bacterium
      1_1_47

<400> SEQUENCE: 21
atgattgctg aacaaatact tttttctcag gggtttggaa cccgccatga atgcacggga      60
cttattcttc aaggccgatt tcatgtcaac ggcactgcag tgactgatcc cgatgaggat     120
atcccaacgg aaaatctgac cttcgaggtt gacggggttg aatggccttt ttttgaaaaa     180
gccatcattc tgctgaacaa acccgagcac tatgaatgct ctttgaagcc aattcatcat     240
ccgagtgtgc tctctctgct gcctccgccc ctgcgtgtca gaaaagtcca gccggtgggc     300
cgtctcgatg aagacaccac aggactgctt ttattaacgg atgacggaaa gctgattcat     360
cggctcacgc accctaagaa acatgtcacc aaaatctatc gggttgcact taagcatccg     420
atcaccgaaa agcaaatcgc tcatctcctt aagggagtac agcttgcaga ttcgccggat     480
atcgtcaaag ccgtcagctg cgaaaaagtc tccgaactcg tcattgatct cggcattacg     540
caaggcaagt atcatcaggt caaacgcatg atggctgccg tatctaatcg agtcgtcgcg     600
ctggaacgaa tccgtttcgg aaacctctcg ctgccggaag acttaaaacc gggagaatgg     660
acctgggtca atccgtcaa ggaaattacc ggatga                                696

<210> SEQ ID NO 22
<211> LENGTH: 912
<212> TYPE: DNA
<213> ORGANISM: Clostridium hathewayi DSM 13479
<220> FEATURE:
<223> OTHER INFORMATION: isolated from gut, Clostridium hathewayi DSM
      13479

<400> SEQUENCE: 22
atgagcctgc gaaccatgat caaaggagga tttacaatga aaaaaatgat cgctgggtta      60
ttgtgtggct gtatgatcgc ggcttctttta acgggctgtg aaaagcgcc tgcttccgat     120
ggcggtgcga cagaaaaggc tgccggtgcg gaggcagaaa aagcagcgga taaaaccgaa     180
gcttcttccg attccggttc caaagtaatt aatgtctggt cgtttaccga cgaagtgcca     240
aagatgattg aaaagtacaa agaaatgcat ccggattttg attatgagat taaaacaaca     300
attattgcga ctactgatgg cgcgtaccag ccggcgctgg atcaggcact ggcatccggc     360
ggcagtgatg cgccggatat ctactgtgcg gaagccgcat ttgtcctgaa atatacgcag     420
ggtgacgcca gccgttatgc cgcgccatac gaagatctgg gaattgacgc ggatggtaag     480
attaaatcct ctgagatcgc acagtatgcg gtcgatatcg aacgaatcc tgacggtaaa     540
gtggtggcgc tgggctacca ggcaaccggc ggagcgttta tctatcgccg ttccatcgcc     600
aaggacacct ggggaaccga tgatccgaag gaaattggtg caaagcttgg cgcaggcacc     660
aatgactgga cacaattctt taacgcggca gaagagctga agggcaaggg ctacggcatt     720
gtatccggcg acggagatat ctggcacgca gtggaaaaca gctcggacaa aggctggatt     780
gtggacggaa aattaaacat cgatccaaag agagaggcat ttctggattt atccaagaag     840
ttaaaggaca acggctatca caatgacaca caggactggc aggatgcggg gtttgccgat     900
atgaagggag aa                                                         912

<210> SEQ ID NO 23
<211> LENGTH: 483
```

<212> TYPE: DNA
<213> ORGANISM: Fusobacterium sp. 7_1
<220> FEATURE:
<223> OTHER INFORMATION: isolated from gut, Fusobacterium sp. 7_1

<400> SEQUENCE: 23

```
atggaaaata taatgacaat atttcaacaa tatggtggag tagtatttgg agttttaggg      60
gcagctcttg cagttttatt atctggtatt ggttcagcaa gaggagttgg aattgcaggg     120
caggcagcag caggtttagt tattgatgaa cctgaaaagt ttggtaaagc tatggtactt     180
caacttttac ctgaaacaca aggactttat ggatttgtaa tagggctttt tattatgttt     240
agacttacac ctgaaatgac aatagcagaa ggtttgtatt tgttaatggc aggacttcca     300
gttggttttg ttggattaag atcagctcta tatcaagggc aagttgcagt agcaggtatt     360
aacattctag caaaaaatga acctcatcaa acaaaaggaa taatacttgc agtaatggtt     420
gaaacttatg caattttagc atttgctatg tctttcctat tactaaatca agtaaaattt     480
taa                                                                   483
```

<210> SEQ ID NO 24
<211> LENGTH: 1155
<212> TYPE: DNA
<213> ORGANISM: Unknown
<220> FEATURE:
<223> OTHER INFORMATION: isolated from gut, unidentified

<400> SEQUENCE: 24

```
actgacgctg tgaacatgct ttcggcactg ggtgtcatca acggttacga cgatggctct      60
tacaagccgg acgcaactgt tactcgtgcg gagatggcaa agatgatctt tgttgtccgc     120
aacaataaga ttgacgattc ggcttacaag aacaactcta ctaagctgac cgacgtcaac     180
aagcactggg ctgcaggcta catcaagttc tgcgaatccc agggcatcat cgcaggcaag     240
ggcaacaaca agtttgaccc ggatgcaacc gttaccggcg tagaagcagc taagatgctg     300
ctcgtagttt ccggttacga tgctcagaag gctggtctga ccggttctgc atggcagact     360
aacgtcctga gtacgctggc gctgctggca attctggacg cgttaactc cgctctggag     420
tctggcctgc cgcgtcagta cgctgctcag atgatctaca acaccctcga cgttaaccgt     480
gtaaagtggt ccgaagactc caagtccttc gacgacgttc tcaacggcgg cgttaaggag     540
actgttggta aggcttacat gggcctgtgc tacgattacg gtactctgac cgaaatcgat     600
accgattctc tgaccatcaa gctcgactct gactacgact ctgacaacta ccacaactct     660
gaccgcaact acaagggtgg cgacaaggtt tccttcacca aggtaggcga ggactacacc     720
gcactgctcg gccagaaggt taaggtaatg ttcaaggacg gcaagaccaa caatgttctg     780
ggcgtatact ccatctctga caacaaggtt tacaccaccc ggatgaacaa ggttgagctg     840
gacggtcaga agatcaagtt cggcggtact tcttactctg ttgataacac caagaagatc     900
gacctgacct tcatcggcgt taacggcacc aagaacgaga ctgttggtat tgcttacttt     960
gacaaggacg gcgcactgaa cgacgataag tccaacggtg taacttctct gtctgaggta    1020
accttcgttg ataccgacgg caacaacaag atcgataccg ctctggttat cgagaaggtt    1080
gctggtgaag ttaccaacgt tgcttccgac aagatcacct tcgctggtaa gacctataag    1140
ttcgctgacg agcag                                                     1155
```

<210> SEQ ID NO 25
<211> LENGTH: 768
<212> TYPE: DNA

```
<213> ORGANISM: Bacteroides sp. 2_1_56FAA
<220> FEATURE:
<223> OTHER INFORMATION: isolated from gut, Bacteroides sp. 2_1_56FAA

<400> SEQUENCE: 25
atgcgggtag gttccgtaca agaaacggag caagagaaag gctgtgccca tttcctcgaa      60
cacgtaactt tcggcggtac ccgccatttt cctaaacgct ctttagtaga gtacctcgag     120
tccttaggaa tgaagtacgg acaagatatc aacgctttca ccggtttcga ccgtacaatc     180
tatatgttcg cagttcccac cgatcatgcc aaagacgaag ttctcgatcg ttcattacta     240
atcctatgcg attggttgga cggtgtcact atagatccgg aaaaagtaga gaatgaaaaa     300
ggaatcattc ttgaagaact acgcggattc gatccggaag acgatttcta tccgctcaaa     360
atcggacaag gcatattcag tcaccgtatg cctttgggca aacagacga tatccgcaag     420 gtcaccccgc aagtgctcaa aaattattat cgcaaatggt atgtaccctc tttggcaaca     480
ttggtcattg taggcgacat atctcccttg gagatcgaat ctaaaatcaa agaacgtttc     540
aaatccctgc ccggacgtcc ggtcaatgac ttccggacct accgttaga gtacacccgg      600 ggaatccatc tggcctccat acgagactcg ctgcaaaccc gtacaaaagt cgaattaatg     660
attccacacc cttgcacagt agagcgcacc atggaagacg ctataacaaa gagaaaggac     720
gcctgctcgt cagtgccatt tcttcacgat tccgtgcccg aaactaa                   768

<210> SEQ ID NO 26
<211> LENGTH: 1218
<212> TYPE: DNA
<213> ORGANISM: Faecalibacterium prausnitzii A2-165
<220> FEATURE:
<223> OTHER INFORMATION: isolated from gut, Faecalibacterium prausnitzii
      A2-165

<400> SEQUENCE: 26
atggataaaa tcagtgcaag cgttcttta aaaggcctgg ccccggaggg ctttgccgat       60
gaggcagcca tcgaccttgt gaccaccgac agccgcgagg tgcgcccgg gtgcatcttt      120 gtggcgttcc ccggtgaaaa atttgacggc cacgatttcg cggccaaagc actggaagaa     180
ggggccgaat atgtcgtcct caaccacccg gtgaaggatg tccggcgggg aagtgtttc      240 ctctgcccgg acagctaccg cgccatgatg atgatgggtg ccaactaccg ccgccagttt     300
tcccccaagg tagtgggcgt gacgggcagc gtgggcaaga ccacgaccaa acagatgacc     360
tacgccgcca ttgcgggctt tggcaatacc atcaagaccg agggcaacca gaacaacgag     420
ctgggcctgc cccgcaccat gttccgcatc ggcaaagaga cggagtacgc ggtggtggag     480
atgggcatga gccaccgggg cgagatcgag cggctgagcc gctgcgcccg cccggatgtg     540
ggcatcatca cctgcatcgg cgtgtcgcac attggcaacc tgggcagcca ggagaatatc     600
tgcaaggcca agctggagat ctgcgagggc ctgcccaacg gtgccccgct ggtgctcaac     660
ggggatgacc cgttcctgcg gccgcgaag ctgccggagc atgtccaccc ggtctggttc     720
agcctggggg atgagaacgc ggacgtctgc gccctgaaca tccggcagga ggacgacggc     780 atgacccttta cgctgaaga ccggggaggaa gacaccaccg aggtgcacat cccggccatg     840
ggccgccaca atgtggccaa cgcgctggcg gcttacgccg ccgccacccg gctgggcctg     900
aacgccaagc gggtcattgc ggggctgagc cagttccagc agaccgggat gcgccagaaa     960
gtgatccaca gcaagggtgt ggatgtcatc gaggactgtt acaacgccaa ccccgacagc    1020
atgaaagccg cgctggccat gttcaaagag tacccctgca gcgccgcctt tgccctgctg    1080
```

```
ggcgatatgc tggagctggg cgagatcagc ccggaagccc atgagacggt gggcaaacag    1140
gctgcggaat acggcgtgga cttcctcgtg gcctatggcc cggaggcgaa acgcacggcc    1200
caggctgccg cggctgcc                                                  1218

<210> SEQ ID NO 27
<211> LENGTH: 522
<212> TYPE: DNA
<213> ORGANISM: Parvimonas micra ATCC 33270
<220> FEATURE:
<223> OTHER INFORMATION: isolated from gut, Parvimonas micra ATCC 33270

<400> SEQUENCE: 27
gaaatgccaa acaaaaaaat aaatgaagat cctgtagcac ctcaagttgc agcagaaatt     60
atcagagaat acttaaaaac agaaggaaat gcaacacaaa atcttgcaac tttctgtcaa    120
acttatatgg aaccaactgc aacagcattg atggcagaga attttgaaaa aaatgcaatt    180
gataaagatg aatatgcaat gactgcagac cttgaaaaca gatgtgtcga tattattgga    240
aacttatggc atatgaatcc aaaagaagaa cctataggaa catctactgt cggttcatca    300
gaagcttgta tgctaggtgg actagctatg cttttcagat ggaaacatct tgcagataaa    360
gcaggagtta atagattcac caaaaaaaga cctaatcttg taatttcttc aggatatcaa    420
gtatgttggg aaaaattctg tcgctactgg gatattgaaa tgagaactgt tccactagat    480
atggaacatt tatctctcaa tatggataca gtaatggatt at                       522

<210> SEQ ID NO 28
<211> LENGTH: 729
<212> TYPE: DNA
<213> ORGANISM: Unknown
<220> FEATURE:
<223> OTHER INFORMATION: isolated from gut, unidentified

<400> SEQUENCE: 28
atgaagaaaa tgatgaaatt aaatatagcg atttgcgatg acaataaatt agtattggac     60
aatgagaaaa cactgattga agaaacgttg aaagagatgg aataccgta caagatggac    120 aagtatcaaa atcctgaaaa tcttatcaaa atgcatggc aatacgatat ggtgttttta    180
gatgtggaaa tggatgaagt caacggaatt atggcggcgg aaagtattca caatatcaat    240
aaggaatgtt tgctgttttt cgtaaccaac cacgaggttt atatggacta tgctatgaac    300
gagtatgcat tcagattttg ggtaaagcct atgtcgaaag aaaaactgaa atttggggtta   360 gaatcggcat tgaaacggtt ggagagcgat aacaaatgca tagaattcaa caccgacaga    420
aatgttgtga atataccgat aaataaaatt atttttatat gtgccgagaa caaaaagacg    480
actattgtta cggtagatga acaatttgta attgaccgtc cgtataaagt ggtcaaagat    540
atgataaatt catatttctt ctatgagtca cacgcaagtt actatgtgaa cttaaattat    600
gtaaaggcgt attcaccgtc gcacgtcaaa tgcggaatag gaaatcatga atatgaaatt    660
catatgtcgc gaagaaaata tacggaattt aataaatatt ttatagattg gatgggtgaa    720
caaaaatga                                                            729

<210> SEQ ID NO 29
<211> LENGTH: 2529
<212> TYPE: DNA
<213> ORGANISM: Unknown
<220> FEATURE:
<223> OTHER INFORMATION: isolated from gut, unidentified

<400> SEQUENCE: 29
```

-continued

```
atggaaaata taaagataca attcaaggga ataacccgta acactgacga tggaataagt    60
gctgacggtg aatgcatgga gcttattaat gctcgcgtga acaattcaag tatagaaccg   120
atcggtaaac cgataatgct aaagcagact gcacacacgt attccaagat ataccatcat   180
tctatagcta aaaggtatat aggaataacc gagtccggtc agatgtacga aatgccggag   240
gatctttcat cagaaactat aatgaccggt gatttgaagg caaaaagcat agaatttatc   300
ggaaatacaa tatcggtaat aacagatgaa ggtataaggt atatccttt caggaacggt    360
tcatatattt atcttggtga aattcctgac gtacctgagt tcggaattga taaggaagtg   420
aaagctgttt ccgttgaaat agatgaaata tcagataacg atgatgaagt aaggtatgga   480
aacttcacta aagttcttag cgaagctaat aaaaacgggt gttactgcta ttctgcagcg   540
ttttgcgcgg ctttcaggat gtttgacgga agttatatca agtcaactga aatacagatt   600
atattccttg attctgatga ttcagtgact attacttatg gagacaggaa taaccctcag   660
aatattgaat tgtccggagg ttattcaaat cagttttttg ctcaaacaaa ttcgaatgga   720
gttatgcagg cacatatact ttgctttaag ccttcattct ttttgaaga atatgatctt    780
tccgcatgga gcgatattat aataggaata gaaatatttt ccactgataa ttttaggaca   840
agactgcaga aagattattt cggagtctat atatcacagt ttgagatgaa ctgcaagaaa   900
ccgattgaaa gggcgaataa tatcagcctg atgtataata ttacatcgtt aaaacttggt   960
gaaacaaaaa atctgttga tattgacgtt tctatagata accttgcaac ccttccgcac   1020
atggttgaca gttttaacac gcatcattca atattgccaa atcgtctta ttcatataac    1080
aacaggcttc atcttatcgg aataaagaga actctttcaa gtggtgtaag agtgtcttct   1140
accgcaaagg aatatcaatt cctgatacac atatacattc atgcttcaga cggtgataaa   1200
gttatagaga atgggaaat aggtaaatac ataaggacat catcatgta ccctgacagc     1260
agggcataca agatgatcat atatagatat gaatataatg ttccggttgt aggaatccag   1320
attgatttga aaaaagcga ttactttgat ttttcatttt attgtaagga atatgaatat   1380
gaaagaggaa gcgttaaaca aaatacaggg ttctttgacg ttataaagat gagcgatttt   1440
gaaagcatgg aagttggaga acaacagac aacatggatt acgaaaaagg aaatgtaatg    1500
tatgtttcaa acctgaacaa tccgtttttc tttcctgctg accaggttta tcagttcaat   1560
actgatattg tcggagtaca gtcaaacgtc gtggccctat ctcaaggaca gttcggccag   1620
ttccctcttt acgtattcac caaagacggt atatacgcca tgaatgtagg aagcggagaa   1680
gtcgcatatt caaatcagac acctgttacg cgtgacgtgt gcaacaatcc ggattctata   1740
tgcggacttg atactatggt cgcattttca accgaccgcg gtcttatggt aattaacgga   1800
actgttacag agctaatctc ggaaaagata tacggattcc ttccttcatg ttccgtatct   1860
tcacctataa tagttaagat attagatgta gcttctctgg gtgacgatat atcaagcgtt   1920
gtgttccctg actatataga agaagcaaag ataggataca actatgaagc aaaggaaatt   1980
gttgttgcaa acatgaattt tccttattcg tacgtttatt cattgaagac cggggaatgg   2040
cataaaatat cacagaatat agattcattc gtcaactcct accctacac gtgggctgta    2100
agcggaaacc agatacttga ccttaacaac acccatagaa gcgtgtctac catagcactt   2160
ataagcaggc ctatcaagat gggtactctt acacacaagc gaatacttca gacagcttta   2220
aggggaatag taaaaagaag cctttccgac ctttacataa aggtgagcc ggtaatgttc    2280
agaggtgaca cggtagatat attttctgac gtaggaatgt atgtacttgc ttcaaatgat   2340
```

```
gccgaacatt ttgagctggt tgcaaagaag gaaaagatgg tagatataag ggacctggtg    2400
acgaagatga acaagagcaa gccttataaa tacttcatgg tatgtcttgt aggaggtgta    2460
aggactgacg tttcaataaa ctacatagaa atgaatgtgg atgaaagctt tacgaacagg    2520
cttagatag                                                            2529

<210> SEQ ID NO 30
<211> LENGTH: 147
<212> TYPE: DNA
<213> ORGANISM: Unknown
<220> FEATURE:
<223> OTHER INFORMATION: isolated from gut, unidentified

<400> SEQUENCE: 30
aggattgcag ccctctttcg agcggctttg cagggagggg tcttgccccc tccgcgggc       60 gtcagggaca ccgccccta cagcaccgac gcgcccggca ggcgggcact gacgagaatt    120
ttcacgaaaa acatcggttt tccgtaa                                         147

<210> SEQ ID NO 31
<211> LENGTH: 543
<212> TYPE: DNA
<213> ORGANISM: Clostridium hathewayi DSM 13479
<220> FEATURE:
<223> OTHER INFORMATION: isolated from gut, Clostridium hathewayi DSM
      13479

<400> SEQUENCE: 31
atgagcatgc aacaagatga agatatgttg ttacagtcga tttatgaaga gtatcaggga     60
acgctccgcc ggattgcgag agcgctgaat gttcccaaca tggaactgga agatgtagtt    120
caggaaacgt ttattgctta ttttaggaag tattcattaa catggtcgcc aacgcttaag    180
aaggcgatgc tggtgaaaat cttaaaggga aaagcaattg actgtctcag aaagaatgga    240
cattatgaaa aggtcagtct tgatgaggag aattcaataa gatgtattga gatgctgacc    300
acctatgtgg taacagatcc cattgatatt attatcagtg aggaatcgat acagaggatt    360
actacggaaa tagccaatat gaggcaggaa tggaaagaga tggctgtttt gtattttctc    420
gagcagagaa ccattccgga gatttgtgaa atgctggaga taccgggaac ggtttgccgc    480
tcccggattt acaggacaag aatgtgtctg aaaaagattc tcggaccgaa atacgatatt    540
taa                                                                  543

<210> SEQ ID NO 32
<211> LENGTH: 29
<212> TYPE: DNA
<213> ORGANISM: Unknown
<220> FEATURE:
<223> OTHER INFORMATION: primer

<400> SEQUENCE: 32
aagaatggag agagttgtta gagaaagaa                                       29

<210> SEQ ID NO 33
<211> LENGTH: 26
<212> TYPE: DNA
<213> ORGANISM: Unknown
<220> FEATURE:
<223> OTHER INFORMATION: primer

<400> SEQUENCE: 33
ttgtgataat tgtgaagaac cgaaga                                          26
```

<210> SEQ ID NO 34
<211> LENGTH: 30
<212> TYPE: DNA
<213> ORGANISM: Unknown
<220> FEATURE:
<223> OTHER INFORMATION: primer

<400> SEQUENCE: 34
aactcaagat ccagaccttg ctacgcctca                                    30

<210> SEQ ID NO 35
<211> LENGTH: 24
<212> TYPE: DNA
<213> ORGANISM: Unknown
<220> FEATURE:
<223> OTHER INFORMATION: primer

<400> SEQUENCE: 35
ttgtaagtgc tggtaagggg attg                                          24

<210> SEQ ID NO 36
<211> LENGTH: 26
<212> TYPE: DNA
<213> ORGANISM: Unknown
<220> FEATURE:
<223> OTHER INFORMATION: primer

<400> SEQUENCE: 36
cattcctaca taacggtcaa gaggta                                        26

<210> SEQ ID NO 37
<211> LENGTH: 30
<212> TYPE: DNA
<213> ORGANISM: Unknown
<220> FEATURE:
<223> OTHER INFORMATION: primer

<400> SEQUENCE: 37
agcttctatt ggttcttctc gtccagtggc                                    30

<210> SEQ ID NO 38
<211> LENGTH: 20
<212> TYPE: DNA
<213> ORGANISM: Unknown
<220> FEATURE:
<223> OTHER INFORMATION: primer

<400> SEQUENCE: 38
aatgggaatg gagcggattc                                               20

<210> SEQ ID NO 39
<211> LENGTH: 21
<212> TYPE: DNA
<213> ORGANISM: Unknown
<220> FEATURE:
<223> OTHER INFORMATION: primer

<400> SEQUENCE: 39
cctgcaccag cttatcgtca a                                             21

<210> SEQ ID NO 40
<211> LENGTH: 26
<212> TYPE: DNA
<213> ORGANISM: Unknown

-continued

```
<220> FEATURE:
<223> OTHER INFORMATION: primer

<400> SEQUENCE: 40
aagcctgcgg aaccacagtt accagc                                          26
```